(12) United States Patent
Bostrom et al.

(10) Patent No.: US 6,758,090 B2
(45) Date of Patent: Jul. 6, 2004

(54) METHOD AND APPARATUS FOR THE DETECTION OF BUBBLE POINT PRESSURE

(75) Inventors: Neil Bostrom, Danbury, CT (US); Douglas D. Griffin, Bethel, CT (US); Robert L. Kleinberg, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/206,499

(22) Filed: Jul. 26, 2002

(65) Prior Publication Data

US 2002/0194907 A1 Dec. 26, 2002

Related U.S. Application Data

(63) Continuation-in-part of application No. 09/459,054, filed on Dec. 10, 1999, now Pat. No. 6,490,916, which is a continuation-in-part of application No. 09/094,811, filed on Jun. 15, 1998, now Pat. No. 6,128,949.

(51) Int. Cl.[7] .......................... E21B 49/08; E21B 49/10
(52) U.S. Cl. ................. 73/152.58; 73/152.18; 73/152.23; 73/152.24; 73/152.28; 73/152.54; 73/152.55
(58) Field of Search ............................. 73/19.01, 19.03, 73/19.05, 19.09, 19.1, 61.78, 64.53, 152.18, 152.23–152.28, 152.41, 152.42, 152.54, 152.55, 152.58, 152.51, 152.27, 863.83, 152.16, 61.46–61.47, 61.49, 61.75, 61.79, 64.52, 597, 599, 590; 166/250.01, 252.4, 309; 175/40, 48, 50

(56) References Cited

U.S. PATENT DOCUMENTS

| | | | | |
|---|---|---|---|---|
| 3,974,681 A | * | 8/1976 | Namery | 73/67.5 R |
| 3,974,683 A | * | 8/1976 | Martin | 73/432 PS |

(List continued on next page.)

FOREIGN PATENT DOCUMENTS

| | | | | |
|---|---|---|---|---|
| EP | 610098 A1 | * | 8/1994 | E21B/49/08 |
| GB | 2304906 A | * | 3/1997 | G01N/07/14 |
| GB | 2338563 A | * | 12/1999 | E21B/49/08 |

OTHER PUBLICATIONS

Anderson, A. L. et al. "Acoustic of Gas–Bearing Sediments I. Background". *Journal of the Acoustical Soc. of America*, vol. 67, pp. 1865–1889 (1980).

(List continued on next page.)

*Primary Examiner*—Hezron Williams
*Assistant Examiner*—David A. Rogers
(74) *Attorney, Agent, or Firm*—Jody Lynn DeStefanis; William B. Batzer; John J. Ryberg

(57) ABSTRACT

The present invention discloses a method and apparatus to detect bubbles in a fluid sample to determine if gases are present, wherein an ultrasonic source is used and its properties monitored. Fluctuations in the ultrasonic source's electrical properties indicate the presence of bubbles/gas. Alternatively, the ultrasonic source may be used to cavitate the sample and induce the nucleation of bubbles. In such a system/method, bubbles may be detected by either (1) monitoring the ultrasonic source properties, (2) monitoring the compressibility of the sample, (3) monitoring the sample properties, including harmonics and subharmonics. The method and apparatus disclosed herein may be used in a borehole such as with a sampling means (including either a flowing sample or a stationary sample) or in a surface lab.

33 Claims, 23 Drawing Sheets

U.S. PATENT DOCUMENTS

| | | | | |
|---|---|---|---|---|
| 4,092,858 A | * | 6/1978 | Edgerton | 73/170 A |
| 4,130,010 A | * | 12/1978 | Wonn | 73/19.03 |
| 4,369,100 A | * | 1/1983 | Sawyer | 204/157.1 S |
| 4,571,693 A | * | 2/1986 | Birchak et al. | 702/54 |
| 4,583,595 A | * | 4/1986 | Czernichow et al. | 166/264 |
| 4,622,463 A | * | 11/1986 | Hill | 250/259 |
| 4,689,986 A | * | 9/1987 | Carson et al. | 73/19.03 |
| 4,722,224 A | * | 2/1988 | Scheller et al. | 73/599 |
| 4,782,695 A | | 11/1988 | Glotin et al. | 73/155 |
| 4,860,581 A | * | 8/1989 | Zimmerman et al. | 73/155 |
| 4,964,101 A | * | 10/1990 | Liu et al. | 367/31 |
| 5,097,698 A | * | 3/1992 | Wood et al. | 73/54 |
| 5,167,149 A | | 12/1992 | Mullins et al. | 73/155 |
| 5,201,220 A | * | 4/1993 | Mullins et al. | 73/152.42 |
| 5,269,180 A | * | 12/1993 | Dave et al. | 73/152.06 |
| 5,329,811 A | | 7/1994 | Schultz et al. | 73/155 |
| 5,473,939 A | | 12/1995 | Leder et al. | 73/155 |
| 5,622,223 A | * | 4/1997 | Vasquez | 166/264 |
| 5,635,631 A | | 6/1997 | Yesudas et al. | 73/61.46 |
| 5,723,773 A | * | 3/1998 | Bryan | 73/61.75 |
| 5,741,962 A | | 4/1998 | Birchak et al. | 73/152.16 |
| 5,769,608 A | * | 6/1998 | Seale | 417/53 |
| 5,785,131 A | * | 7/1998 | Gray | 175/46 |
| 5,799,733 A | * | 9/1998 | Ringgenberg et al. | 166/264 |
| 6,128,949 A | | 10/2000 | Kleinberg | 73/152.18 |
| 6,490,916 B1 | | 12/2002 | Goodwin et al. | 73/152.58 |

OTHER PUBLICATIONS

Anderson, A. L. et al. "Acoustics of Gas–Bearing Sediments II. Measurements and Models". *Journal of the Acoustical Soc. of America,* vol. 67, pp. 1890–1903 (1980).

Burdic, W. S. "Underwater Acoustic System Analysis". Prentice–Hall, QC 242.2–, B87 (1991).

Flynn, H. G. "Physics of Acoustic Cavitation in Liquids". *Physical Acoustics,* vol. 1, Part B. (1964).

Leighton, T. G. "The Acoustic Bubble". Academic Press, Chap. 4.4.7, QC 242.2, L45 (1994).

Pearsall, I. S. "Cavitation". Mills & Boon (1972).

Towle, D. M. et al. "Absorption and Velocity of Ultrasonic Waves of Finite Amplitude in Liquids". *Journal of the Acoustical Society of America,* vol. 27, pp. 530–533 (1955).

* cited by examiner

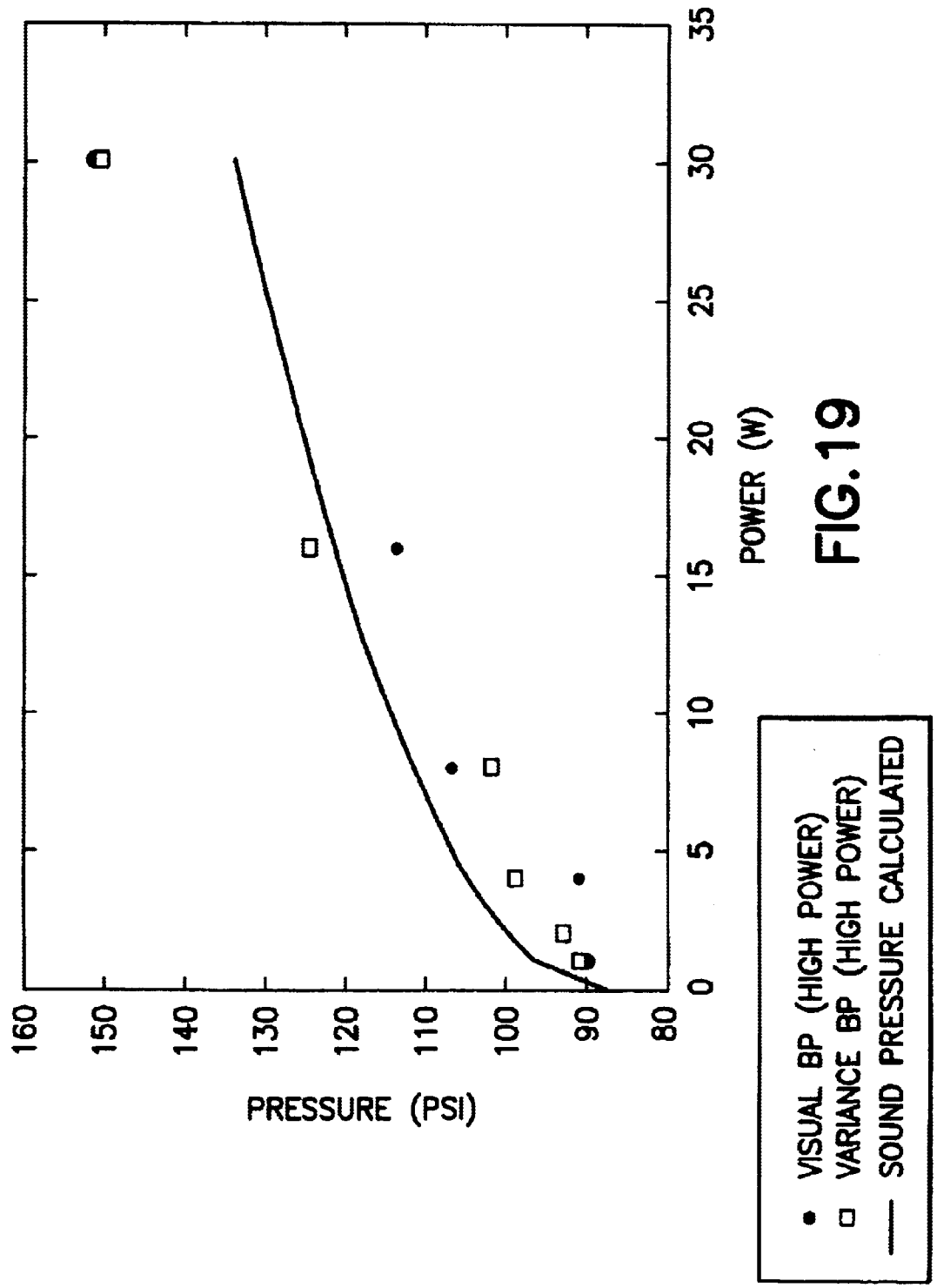

# METHOD AND APPARATUS FOR THE DETECTION OF BUBBLE POINT PRESSURE

REFERENCE TO PRIOR APPLICATIONS

This is a continuation-in-part of U.S. application Ser. No. 09/459,054, filed Dec. 10, 1999, now U.S. Pat. No. 6,490,916 (the '916 Patent), which is a continuation-in-part of U.S. application Ser. No. 09/094,811, filed Jun. 15, 1998, now U.S. Pat. No. 6,128,949 (the '949 Patent). The '916 and the '949 Patents are incorporated herein by reference in their entireties.

FIELD OF THE INVENTION

This invention relates to a method for the detection of gases in a flowing sample and, more particularly, to the use of ultrasound to induce the nucleation of bubbles and identify the bubble point in a formation fluid.

BACKGROUND OF THE INVENTION

Thermodynamic properties of reservoir fluids are of great interest to reservoir engineers. One important property is the bubble point pressure (or simply "the bubble point"). Bubble point is the pressure at which gas evolves as bubbles in a fluid sample and is characterized by slowly forming thermodynamically stable bubbles. If the borehole pressure drops below the bubble point during production, gas bubbles will form in the porous reservoir rock, dramatically decreasing the relative permeability to the oil phase. Knowledge of the bubble point is also useful in determining the composition of the hydrocarbon mixture in the reservoir.

Quantitative bubble point determination is currently performed on fluid samples that have been brought to the surface. The captured fluid sample is sent to a PVT Laboratory for testing. There, the sample is placed in a cylinder, the volume of the cylinder is incrementally increased, and the pressure is monitored. Using this method, the bubble point is the pressure at which a break (knee) appears in the pressure versus volume (P-V) curve as shown in FIG. 1. This change of slope ($\Delta(dP/dV)$) is taken to be indicative of the bubble point.

However, PVT techniques have been found to be slow and unreliable because bubbles do not readily form at the thermodynamic bubble point of the liquid. Even when the gas phase is thermodynamically stable at a given temperature and pressure, a gas bubble may be unable to form because its surface free energy exceeds the free energy difference of the bulk phases. This phenomenon accounts for the supercooling, superheating, or supersaturation generally observed at first order phase transitions, as described by classical nucleation theory. In order to minimize the error associated with nucleation, bubble point measurements are made by changing the volume very slowly, typically over a period of an hour.

Wireline formation sampling and testing tools, such as the Schlumberger MDT, extract fluids from subsurface formations adjacent to a borehole by pumping fluids through a flowline. A primary goal of these tools is to capture samples for transport to the surface. However, one problem of these fluid sampling processes is the possibility that the fluid extracted and processed by the tool may not be representative of in-situ formation fluid. For example, if dissolved gas exists in the formation, the gas might evolve during sampling leading to erroneous measurements of fluid mobility as well as erroneous indications of free gas. Because optimal bubble point measurement techniques require identification of the first appearance of gas in the flow stream, these tools may result in unreliable bubble point measurements.

In-situ bubble point measurement using PVT (i.e., compressibility) theory is described in commonly owned U.S. Pat. No. 4,782,695 to Gotin et al., which is incorporated herein by reference in its entirety. Some problems and uncertainties of this method have been identified and partially addressed in U.S. Pat. No. 5,635,631 to Yesudas et al., which is incorporated herein by reference in its entirely.

Additional in-situ bubble point detection methods based on PVT measurements are described in U.S. Pat. No. 5,329,811 to Schultz et al. and U.S. Pat. No. 5,473,939 to Leder et al., which are incorporated herein by reference in their entireties. These methods are based on measuring pressure in the flowline as a function of flowline volume.

Another gas detection method for fluid sampling tools is discussed in U.S. Pat. No. 5,741,962 to Birchak et al. (the '962 Patent). The '962 patent discloses a method of determining properties of reflected and transmitted acoustic waveforms following a short initial acoustic impulse. The time delays and amplitudes of the acoustic waveforms are analyzed to find several properties of the fluid in the flowline, including the presence of bubbles.

The '962 Patent monitors fluid acoustic impedance by measuring the amplitude of waves reflected from a fluid-solid interface necessitating the use of a delay-line crystal and a fluid-solid interface geometry that will produce good reflections. In accordance with the present invention (as discussed below), reflection measurements are not necessary and their attendant limitations are avoided. U.S. Pat. No. 5,741,962 is incorporated herein by reference in its entirety.

It has been found that for some crude oils, the slope of the pressure versus volume graph (as used for PVT techniques) does not change substantially at the bubble point. One reason for this phenomenon is that the compressibility of gas decreases as its pressure increases, thereby decreasing the compressibility contrast between gas and liquid phases. Secondly, the compressibility of the sample is the volume-weighted average of the compressibility of the gas and liquid components. Therefore, if little gas evolves at the bubble point, the average compressibility of the sample may not significantly change, even if the compressibility of the gas phase is considerably greater than that of the liquid. To deal with those situations in which the bubble point is not well marked by a compressibility change, laboratories traditionally use bubble detectors having an optical cell to detect a change in the transmission of light. As bubbles cross the optical path, the transmission of light changes. However, bubbles may form at random locations inside the measurement apparatus and may avoid detection by the optical cell. Optical methods therefore require that the bubbles be transported to the site of the sensor, such as by a stirring mechanism. However, this transport process can be inefficient. In addition, stirring mechanisms tend to be failure-prone and are not the preferred mode of transporting bubbles to the site of the bubble sensor.

Optical means have also been adapted for use in boreholes. For example, one gas detector used in fluid sampling tools is Schlumberger's optical fluid analyzer as described in commonly owned U.S. Pat. No. 5,167,149 to Mullins et al., which is incorporated herein by reference in its entirety.

A method and apparatus for detecting marine gas seeps is disclosed in commonly owned pending U.S. Ser. No. 09/962,063 to Kleinberg et al. filed Sep. 25, 2001. Gas seeps are detected using a locally deployed probe to produce bubbles on or near the ocean floor.

Accordingly, one object of the present invention is to provide a means for making rapid, accurate measurements of bubble point.

Another object of the present invention is to provide a method of nucleating bubbles and sensing the bubble point while operating at a pressure above the bubble point pressure.

Yet another object of the present invention is to provide a gas detector method for validation purposes.

SUMMARY OF THE INVENTION

The present invention discloses a method for determining bubble point pressure and detecting gases under borehole-like conditions (i.e. temperatures and pressures typical of that experienced in borehole environments) by monitoring compressibility of the sample, the properties of the sample or the properties of an ultrasonic transducer in fluid communication with the sample. The ultrasonic transducer may be used to merely detect the presence of gas or bubbles in the sample or it may be used to nucleate bubbles in the sample prior to gas/bubble detection. The use of cavitation induced by an ultrasonic source encourages bubble formation in supersaturated samples. The samples may be captured volume samples or flowing samples. Preferably, the ultrasonic source is a piston transducer and, most preferably, it is a coaxial cylinder cell such as that disclosed in commonly owned pending U.S. Ser. No. 10/167,516 to Liang filed Jun. 12, 2002 (incorporated by reference herein in its entirety).

The properties of the ultrasonic source that are monitored include resonance frequency, voltage, voltage squared, current, current squared, phase angle between current and voltage, power dissipation, or electrical impedance, or combinations thereof. As discussed below, changes in these parameters are reliable indicators of the presence of gas or bubbles in a sample.

When bubbles have nucleated, the compressibility of the sample changes. This compressibility change is evidenced by a change in the slope of the P-V graph as shown in FIG. 1.

In addition, sample pressure, volume, temperature, harmonics and subharmonics are good indicators of the presence of gas or bubbles in the sample. For example, the sample under test will exhibit an increase in temperature at the onset of bubbles. Likewise, the appearance of or change in harmonics or subharmonics in a sample is an indicator of gas and bubble formation.

Varying the power to the ultrasonic source limits the amount of heat transmitted to the sample from the transducer. For example, providing a 0.5 to 30 W pulsed power to the ultrasonic source with 0.1 W applied between pulses continuously agitates the sample while limiting the amount of heat applied to the sample.

Accordingly, in one embodiment of the present invention, a method of fluid analysis for determining phase characteristics of a formation fluid is disclosed, comprising the steps: withdrawing a sample under borehole-like conditions; depressurizing the sample: nucleating bubble formation in the sample by activating an ultrasonic source in fluid communication with the sample; and detecting onset of bubble formation in the sample by monitoring the compressibility of the sample. The sample may be a stationary (i.e., captured volume) sample or a flowing sample. While any ultrasonic source may be used, it is preferably, a piston transducer or a coaxial cylinder cell (such as that disclosed in commonly owned pending U.S. Ser. No. 10/167,516 to Liang filed Jun. 12, 2002). The step of measuring the pressure of the sample at the onset of bubble formation may further comprise the steps of developing a first pressure-volume function of the sample prior to bubble formation; developing a second pressure-volume function of the sample after bubble formation; and extrapolating the intersection of the first and second functions, wherein the intersection represents the bubble point pressure.

In a second embodiment, a method of fluid analysis for determining phase characteristics of a formation fluid is disclosed comprising the steps: withdrawing a sample under borehole-like conditions; depressurizing the sample; nucleating bubble formation in the sample by activating an ultrasonic source in fluid communication with the sample; and detecting onset of bubble formation in the sample by monitoring the temperature of the sample.

In a third embodiment, a method of fluid analysis for determining phase characteristics of a formation fluid is disclosed comprising the steps: withdrawing a sample under borehole-like conditions; depressurizing the sample; nucleating bubble formation in the sample by activating an ultrasonic source in fluid communication with the sample; detecting onset of bubble formation in the sample by monitoring one or more ultrasonic source properties: and measuring the pressure of the sample at the onset of bubble formation.

In a fourth embodiment, a method of fluid analysis for determining the presence of gas in a formation fluid, is disclosed comprising the steps: obtaining a sample under borehole-like conditions, wherein the sample is in fluid communication with an ultrasonic source; and monitoring one or more ultrasonic source properties, wherein fluctuations in the ultrasonic source properties indicate the presence of gas in the sample.

In a fifth embodiment, a method of fluid analysis for determining phase characteristics of a formation fluid is disclosed comprising the steps: obtaining a sample under borehole-like conditions, wherein the sample is in fluid communication with an ultrasonic source; nucleating bubbles in the sample by activating the ultrasonic source; detecting the onset of bubble formation by measuring one or more ultrasonic source properties.

In a sixth embodiment, a method of fluid analysis for determining phase characteristics of a formation fluid is disclosed, comprising the steps: obtaining a sample under borehole-like conditions, wherein the sample is in fluid communication with an ultrasonic source; nucleating bubbles in the sample by activating the ultrasonic source; and detecting the onset of bubble formation by measuring one or more sample properties, wherein the sample properties include pressure, volume, acoustic radiation, transit time, amplitude, harmonics, and subharmonics and combinations thereof.

Enhanced results may be obtained by nucleating the sample twice. In the first nucleation, the sample is rapidly depressurized to obtain a rough estimate of the bubble point pressure determined by monitoring the ultrasonic source properties and/or the sample properties and/or the harmonics/subharmonics. The sample (preferably a fresh sample) is then slowly depressurized over the approximate range of the rough estimate of bubble point pressure. Again, the ultrasonic source properties or sample properties are monitored to identify the sample's bubble point pressure.

Another embodiment discloses an apparatus useful for gas detection and bubble point measurement comprised of: means to withdraw a formation fluid sample having an ultrasonic source; and means to detect the presence of bubbles in said sample by monitoring one or more ultrasonic source properties.

Further features and applications of the present invention will become more readily apparent from the figures and detailed description that follows.

BRIEF DESCRIPTION OF THE DRAWINGS

FIG. 19 is a graphical representation showing the pressure of the first appearance of bubbles versus acoustic power.

DETAILED DESCRIPTION

Bubble Nucleation

In accordance with the present invention, ultrasonic cavitation may be used to obtain bubble point information by stimulating bubble formation. Cavitation has been considered to be impossible using traditional methods when fluid pressure is high. Because pressure in the sampling tool flowline may be as high as 20,000 psi, it would appear that cavitation is not a viable method for creating bubbles in a borehole using conventional methods. However, for a fluid at the bubble point, modest localized pressure reductions, such as are found in acoustic waves, can lead to efficient evolution of bubbles. Commonly owned U.S. Pat. No. 6,128,949 to Kleinberg discloses this phenomenon and is incorporated herein by reference in its entirety.

Various types of ultrasonic sources or transducers may be suitably employed in the method of the present invention. For example, a piston transducer in the form of a solid cylinder with one of the flat end surfaces being acoustically active may be used. The solid cylinder of this embodiment is generally comprised of a stack of disks. At least one of these disks is a piezoelectric crystal which, when its thickness mode is excited, converts an electrical signal to a mechanical one. Other layers may be comprised of materials having dimensions and properties to aid acoustic coupling of the piezoelectric crystal to the fluid under test. Piston transducers have several advantages. For example, piston transducers are efficient and easy to design and are often commercially available in the desired size and operating frequency. They also often (but not always) produce the highest sound pressure level on their active surface.

Preferably, the ultrasonic source is a coaxial cylinder cell transducer (such as that disclosed in commonly owned pending U.S. Ser. No. 10/167,516 to Liang filed Jun. 12, 2002) that forms part of the flowline. Such a transducer will not interfere with other objectives of the sampling tool that rely on the unimpeded flow of fluid. Coaxial cylinder cell transducers have a geometry similar to that of a bored or hollow rod with the fluid under test along the central (internal) axis of the hollow rod. It focuses its acoustic energy on its axial centerline. Like the piston transducer, it is a layered structure, but the layers are concentric cylinders. At least one of these concentric layers is a piezoelectric crystal that is preferably excited in its hoop mode. Further, a coaxial cylinder cell transducer is relatively immune to erosion because it does not intrude into the flow line. Moreover, it has no parts that substantially move.

Figure 1:
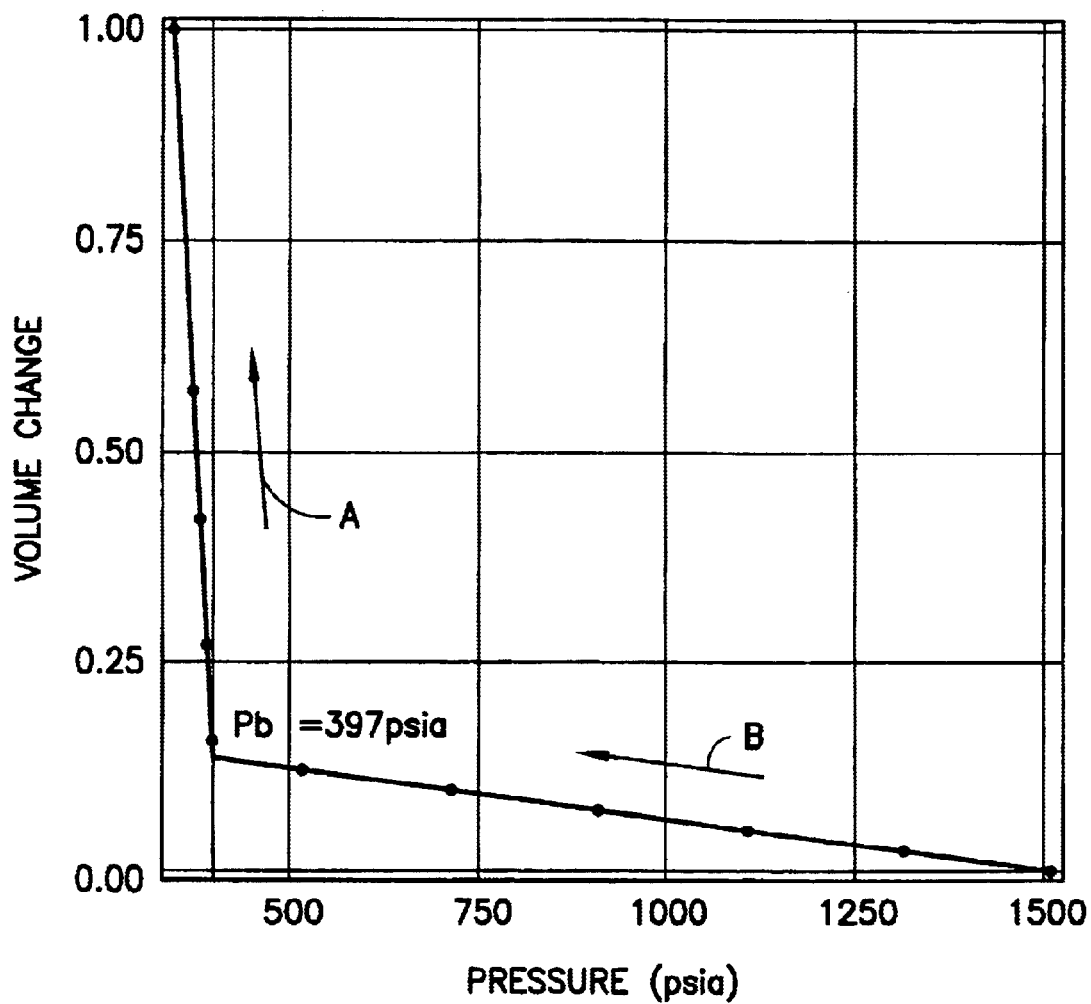
FIG. 1 is a graphical representation of the pressure versus volume determination of a bubble point as performed in the prior art.
Figure 2A:
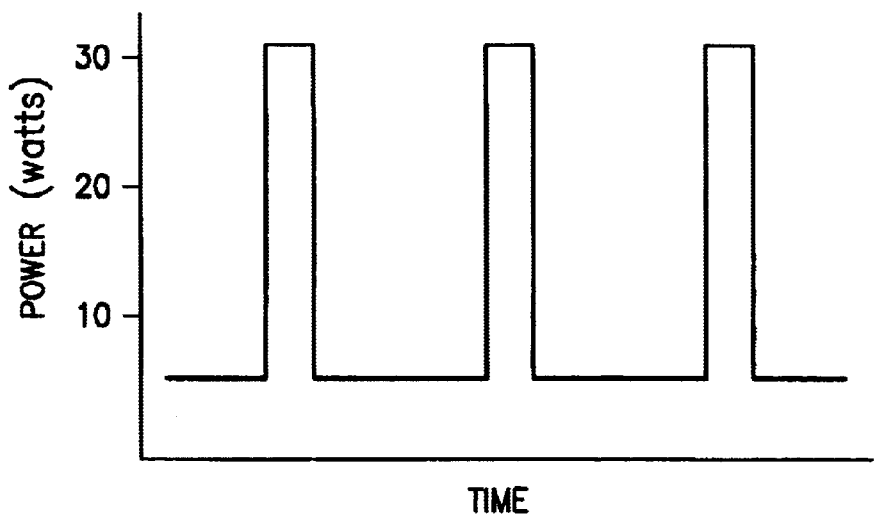
FIGS. 2a through e are graphical representations of the modulation of the power applied to the ultrasonic resonator in accordance with the present invention.

Continuous acoustic energy may be used in bubble point measurements. However, modulating the power to the ultrasonic source can be beneficial in limiting the amount of heat transmitted from the transducer to the sample. This is useful with stationary samples being slowly expanded for precision measurement. Preferentially, low-power acoustic energy is used between the high power pulses to provide continued agitation of the sample. For example, providing 30 W pulsed power to the ultrasonic source with 0.1 W applied between pulses agitates the sample while limiting the amount of heat applied to the sample. One example of modulated power could be 30 W on for 0.5 seconds followed by 0.1 W for 5.5 seconds. This is shown in FIG. 2a. The sequence would be repeated until the sample bubble point had been determined.

Figure 2B:
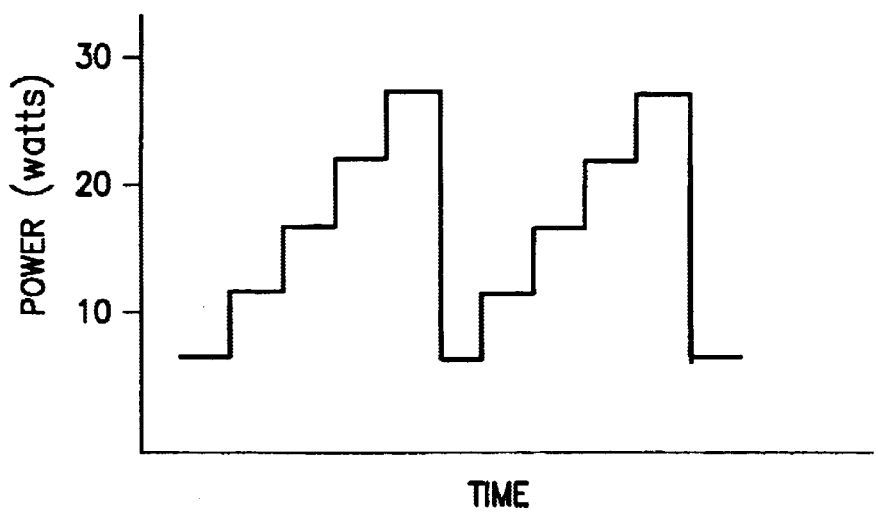
Figure 2C:
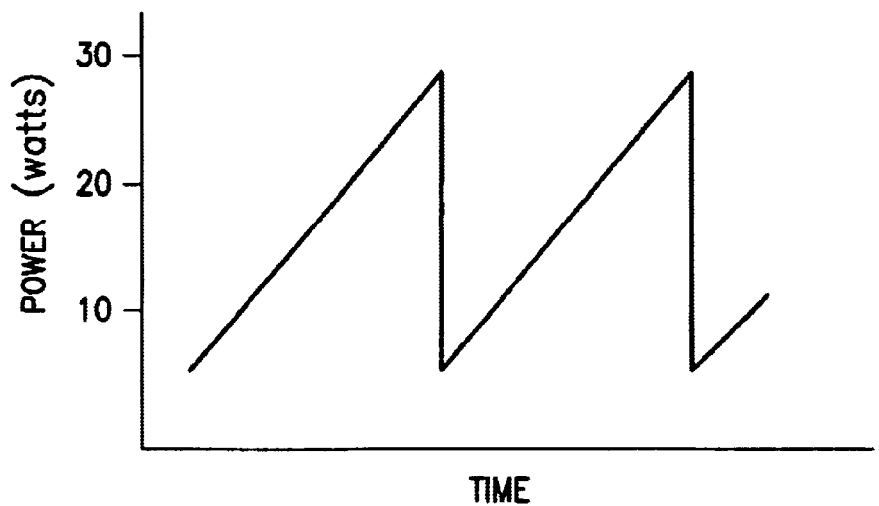
Figure 2D:
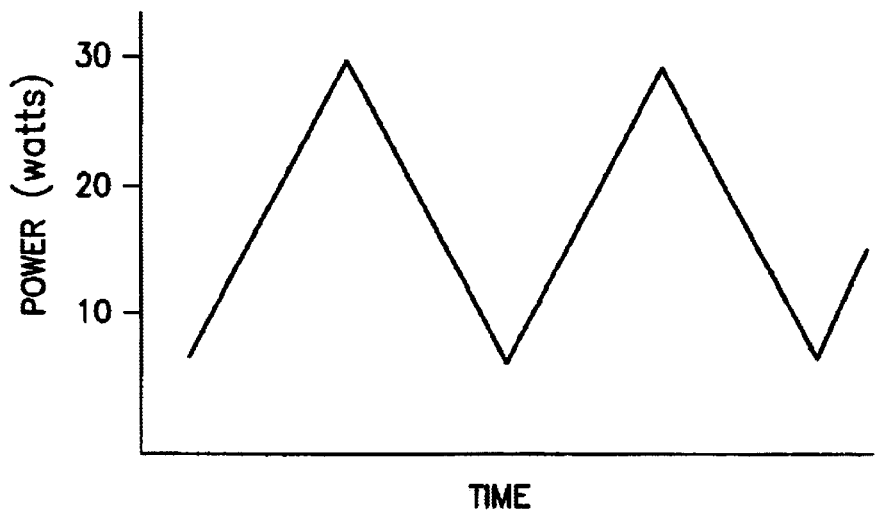

An alternative power modulating technique is a stair-stepped power sequence. Here the pulse begins with low power and increases applied power in step-wise fashion with time. This is shown in FIG. 2b. An example of this is a pulse beginning with 0.2 seconds of 1 W, 0.2 seconds of 5 W, 0.2 seconds of 10 W, 0.2 seconds of 15 W, 0.2 seconds of 20 W, etc. This pulse technique is useful in creating cavitation above the pressure of the fluid. Knowing the power level at which cavitation occurs, allows determination of the bubble point pressure using equation (1), discussed in more detail below. An alternative power modulation method is to use a sawtooth modulation as shown in FIG. 2c. A triangle modulation is shown in FIG. 2d.

Figure 2E:
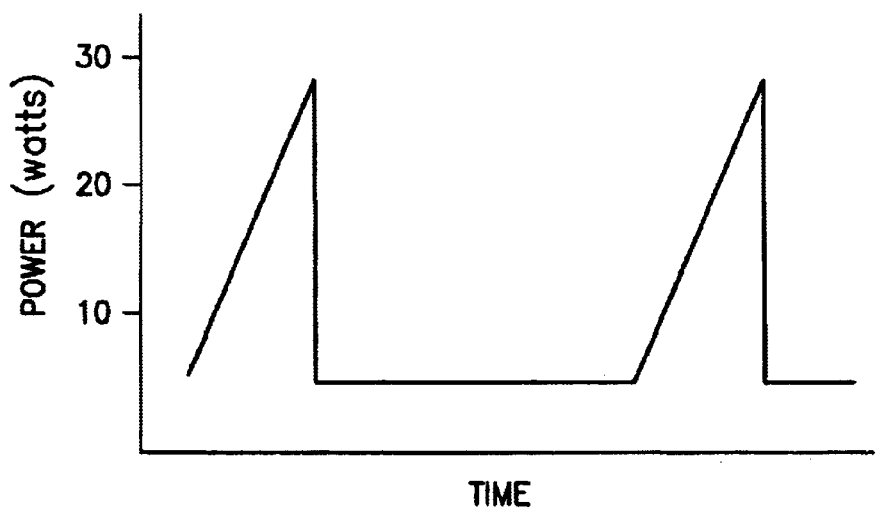

Pulses of step-wise, sawtooth, triangle waves and continuous wave (CW) sequences can be alternated and combined with each other in various amplitudes and durations. One possible example is shown in FIG. 2e. These alternatives help reduce sample heating. These examples are intended to be non-limiting as other pulse sequence designs may be suitably employed.

One reason to use a modulated pulse is to periodically test the bubble point pressure of a liquid without continuously applying the highest power available.

Modulated pulses are useful in testing bubble point pressures above the static pressure of the sample. This is important as fluid sampling is preferentially done by withdrawing a single phase sample. Knowing the margin between the drawdown pressure and the bubble point can be important for setting the flow-line pump speed to avoid evolving dissolved gas.

In applications where it might be advantageous, these modulation methods can also lower the power consumption of the measurement.

Rough surfaces are useful in bubble formation. In accordance with the present invention, it is preferred that the surface of the ultrasonic transducer that contacts the fluid be roughened. In particular, the surface at which the bubble point measurements are made be rough.

Figure 3:
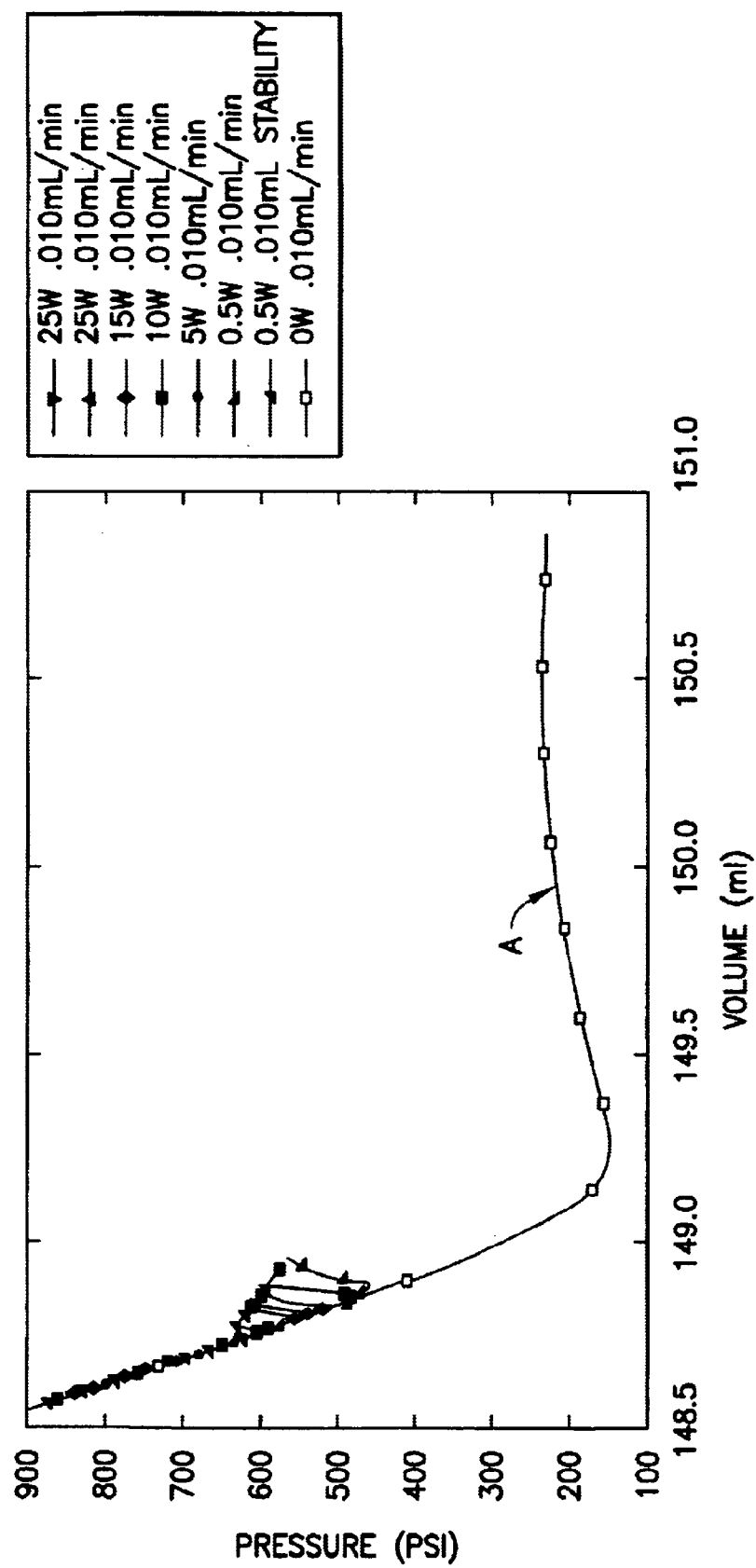
FIG. 3 is a graphical representation of the pressure versus volume characteristics of nitrogen dissolved in water as developed using a piston transducer to induce cavitation wherein the power to the transducer is varied and the depressurization rate is constant.

Turning now to FIG. 3, a sample of nitrogen dissolved in water at high pressure was exposed to ultrasound generated by a piston transducer operating at a resonance frequency equal to 53 kHz. The depressurization rate was maintained at 0.01 cm$^3$/min: the ultrasonic power ranged from 0.5 W to 25 W. Some power-dependent supersaturation was observed at the bubble point; however, this effect was temporary and a clear slope change (indicating a change in compressibility) was observed from which the bubble point could be determined as shown in FIG. 3. The bubble point for this sample was calculated as 650 psig. This bubble point pressure was determined by extrapolating the two-phase P-V line (larger volumes) back into its intersection with the single phase P-V line (smaller volumes).

For comparison purposes, the bubble point of the same sample (nitrogen dissolved in water at high pressure) was determined using conventional PVT technique without ultrasonic cavitation. The volume of the sample was slowly increased while the pressure was monitored. The depressurization rate was 0.01 cm$^3$/min in the 150 cm$^3$ cell, so $\Delta V/V$ was equal to $67 \times 10^{-6}$/min. After four (4) hours of slowly increasing the volume, unsatisfactory results were obtained indicating no clear onset of bubble formation, as shown in FIG. 3 by line A. Accordingly, acoustic cavitation may be used to induce bubble formation and determine the bubble point in samples where conventional methods fail.

Figure 4:
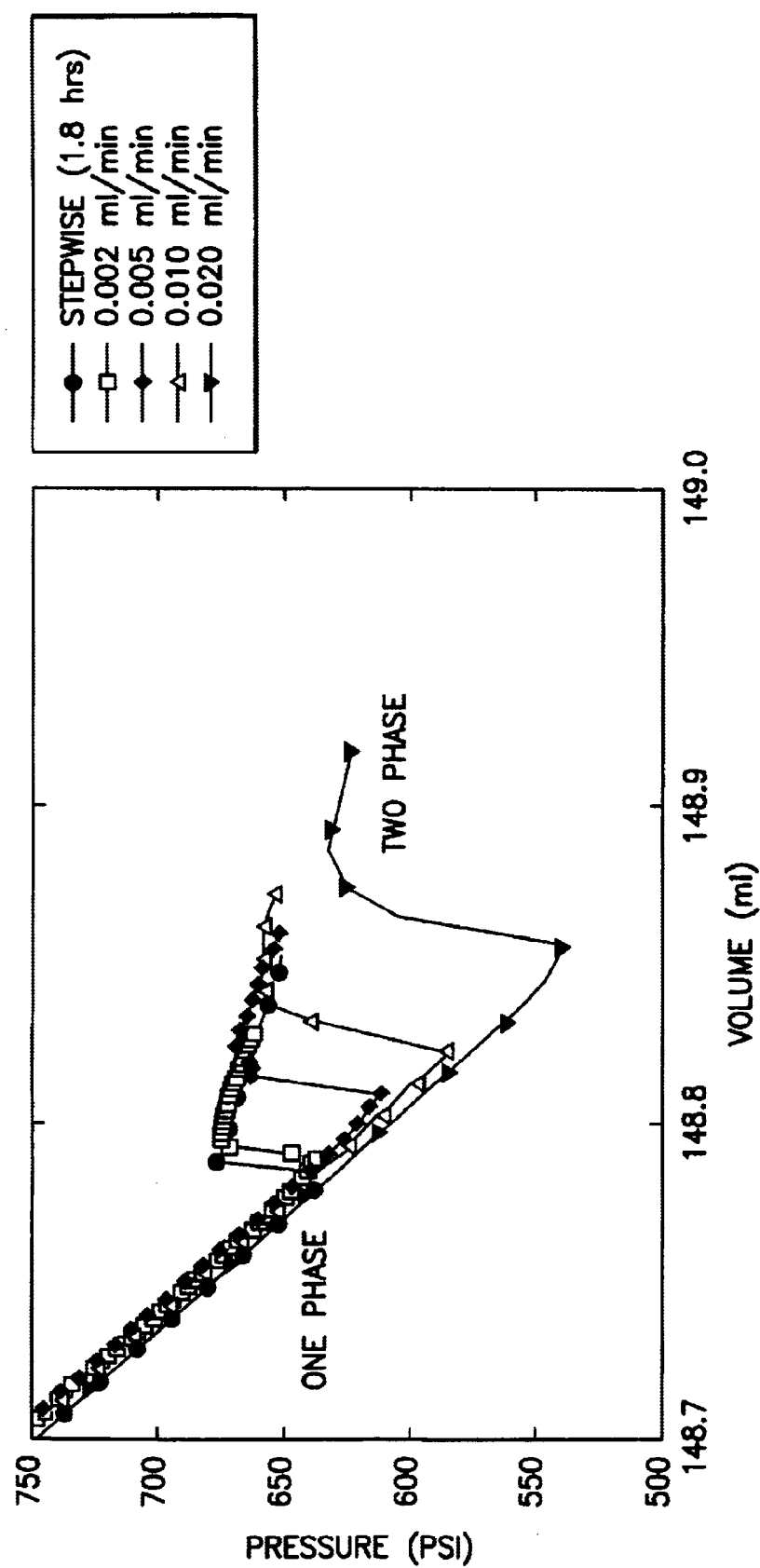
FIG. 4 is a graphical representation of the pressure versus volume characteristics of nitrogen dissolved in water as developed using a piston transducer to induce cavitation wherein the power to the transducer is held constant and the depressurization rate is varied.

FIG. 4 shows another example of this process. In this example, a sample was formed by dissolving nitrogen gas in water. A constant power of 0.5 W was applied to a piston transducer operating at 53 kHz The depressurization rate was varied over the range 0.002 ml/min ($\Delta V/V=14\times10^{-6}$/min) to 0.020 ml/min ($\Delta V/V=140\times10^{31\ 6}$/min). For all depressurization rates, the bubble creation was delayed until the pressure was somewhat below the bubble pressure, which was approximately 690 psig. As the depressurization rate increased, the undershoot below the bubble point increased. However, after nucleation of the first permanent bubbles (which occurred at the bottom of the pressure dip) the pressure versus volume curve returned to a rate-independent trend line reflective of the compressibility of the gas-liquid mixture. As above, this bubble point pressure was determined by extrapolating the two-phase P-V line (larger volumes) back into its intersection with the single phase P-V line (smaller volumes).

Figure 5:
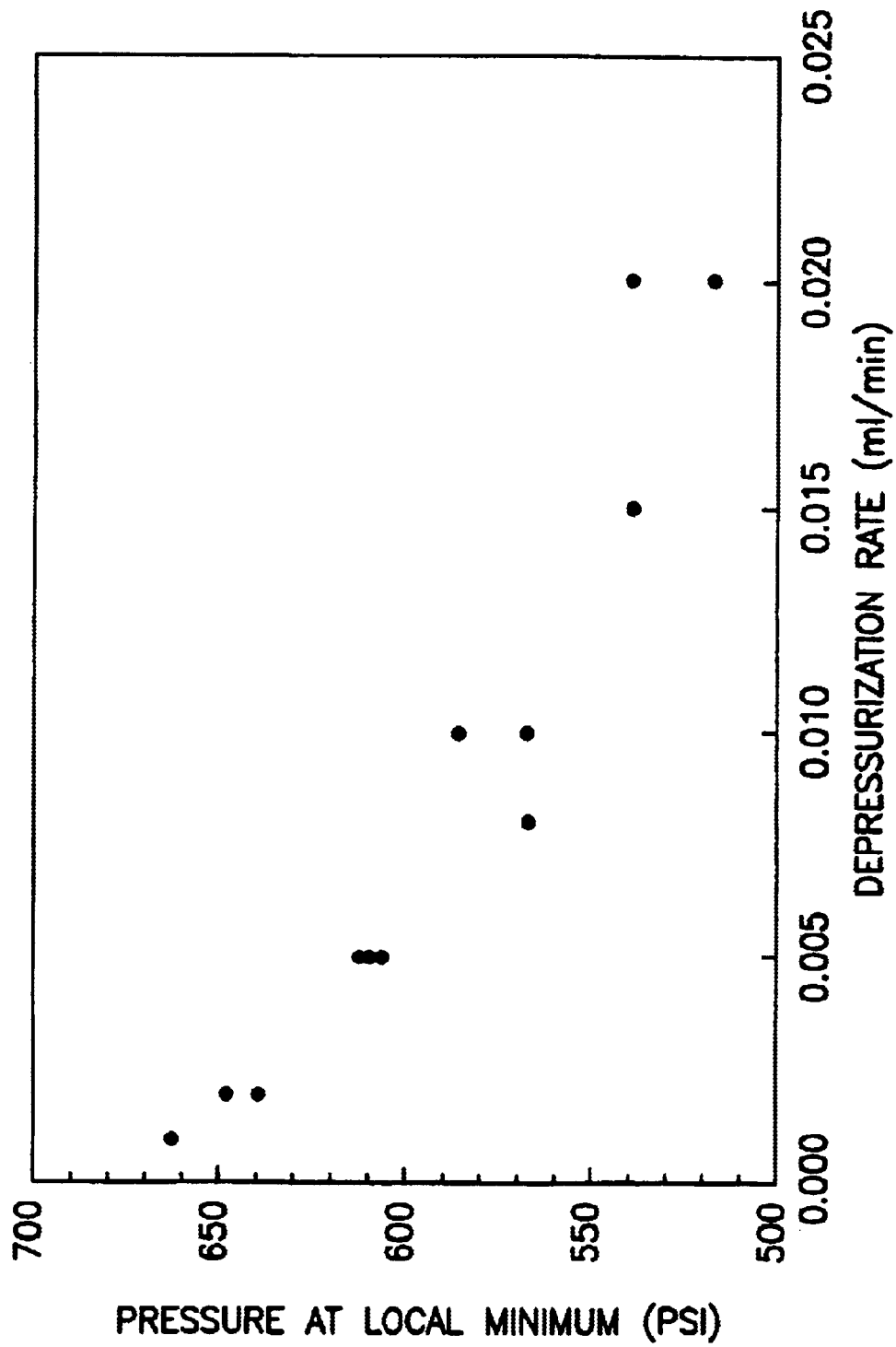
FIG. 5 is a graphical representation of the pressure of the maximum supersaturation versus depressurization rate showing that slow depressurization minimizes supersaturation.

In FIG. 5, the pressure at the local minimum pressure (maximum saturation) is plotted against depressurization rate for the data shown in FIG. 4. The slowest depressurization ($\Delta V/V=7\times10^{-6}$/min) corresponded to a measurement time of 2 hours. The fastest depressurization ($\Delta V/V=140\times 10^{-6}$/min) corresponded to a measurement time of 10 minutes. As shown in this graph, slow depressurization minimizes supersaturation. Note that the supersaturation phenomenon has minimal effect on the accuracy of the bubble point determined by compressibility as disclosed herein.

Figure 6:
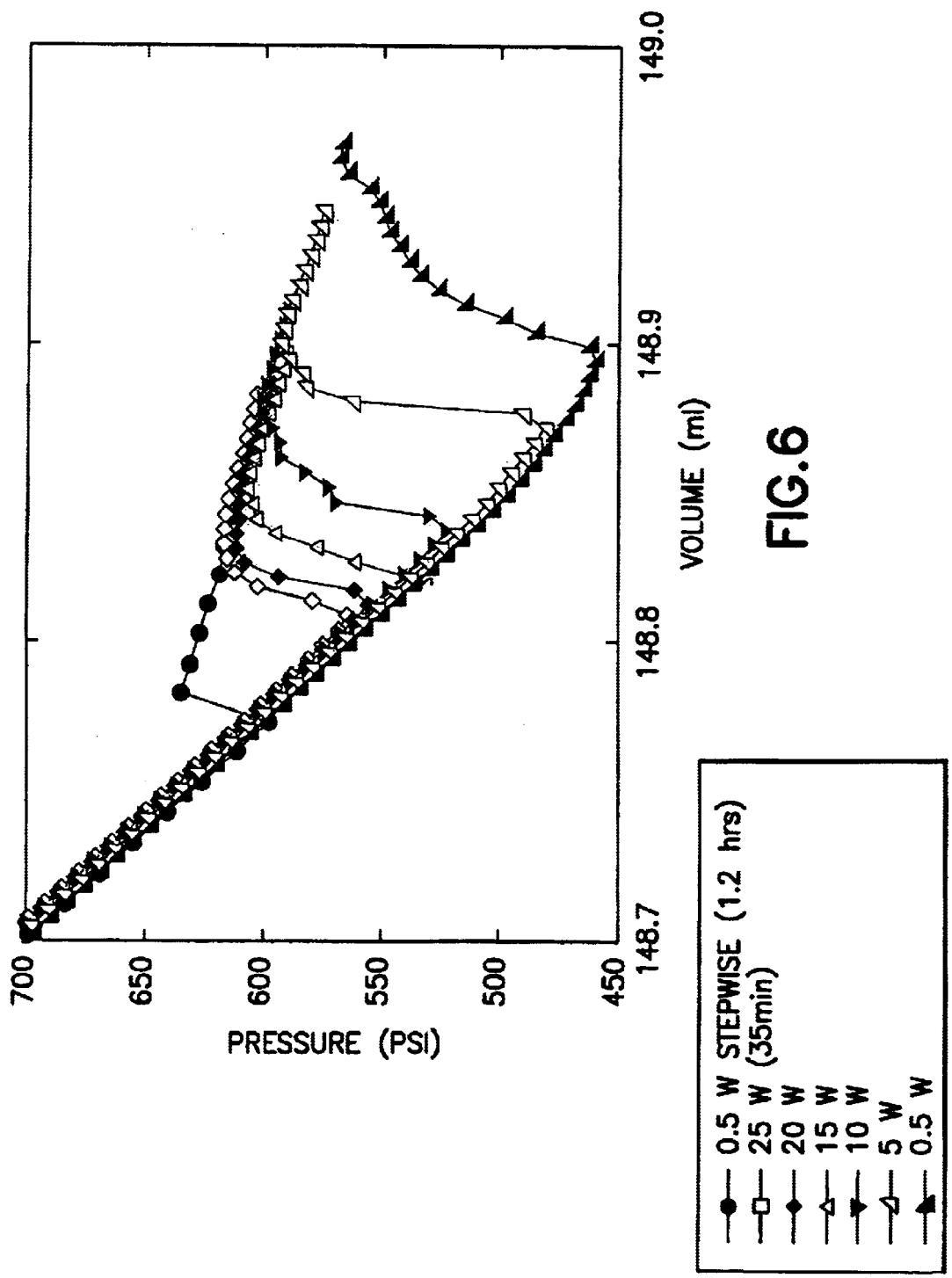
FIG. 6 is a graphical representation of the pressure versus volume characteristics of nitrogen dissolved in water as developed using a piston transducer to induce cavitation wherein the power to the transducer is varied. This graph shows that high power minimizes supersaturation.
Figure 7:
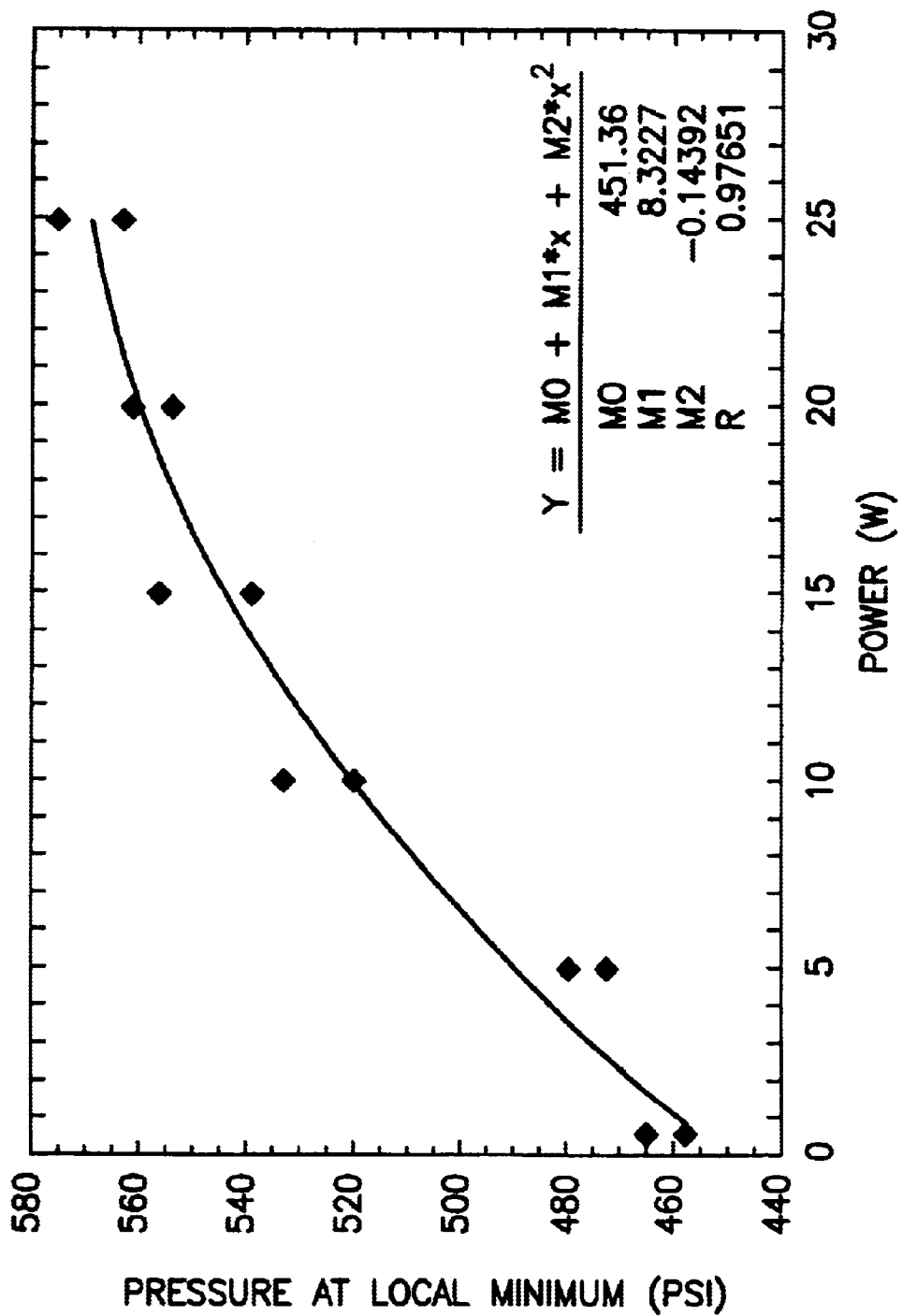
FIG. 7 is a graphical representation of the pressure of maximum supersaturation versus peak ultrasonic power.

As shown in FIG. 3, the apparent pressure-volume behavior at the bubble point is also affected by the transducer power. This effect is shown in more detail in FIG. 6, which shows the pressure versus volume characteristics. At a depressurization rate equal to 0.01 ml/min ($\Delta V/V=70\times10^{-6}$/min), the bubble point was calculated to be 650 psig. The undershoot was the greatest at the lowest power level (0.5 W) and the least at the highest power level (25 W). The powers quoted are pulsed powers wherein 0.5 W was applied between pulses. The duty cycle at high power was 1/60. The pressure at the local minimum as a function of peak power is shown in FIG. 7, which shows the pressure of maximum supersaturation versus peak ultrasonic power. As shown in FIGS. 6 and 7, high power minimizes supersaturation.

FIG. 6 also shows the results of a measurement in which a constant power of 0.5 W (and a depressurization rate of $\Delta V/V=70\times10^{-6}$/min) was used. The sample tested was nitrogen dissolved in water. However, in this example, the pressure was allowed to fully equilibrate after each volume step (shown as a data point). Using the equilibration technique, the undershoot was minimized while measurement time increased (1.2 hours in the present example). For the purposes of this invention, "equilibration" means pressure stabilization (i.e., residual drift of less than about 0.4 psi/min) after each volume step. Accordingly, the onset of bubble formation may be detected after bubble nucleation by monitoring the compressibility of the sample.

Figure 8:
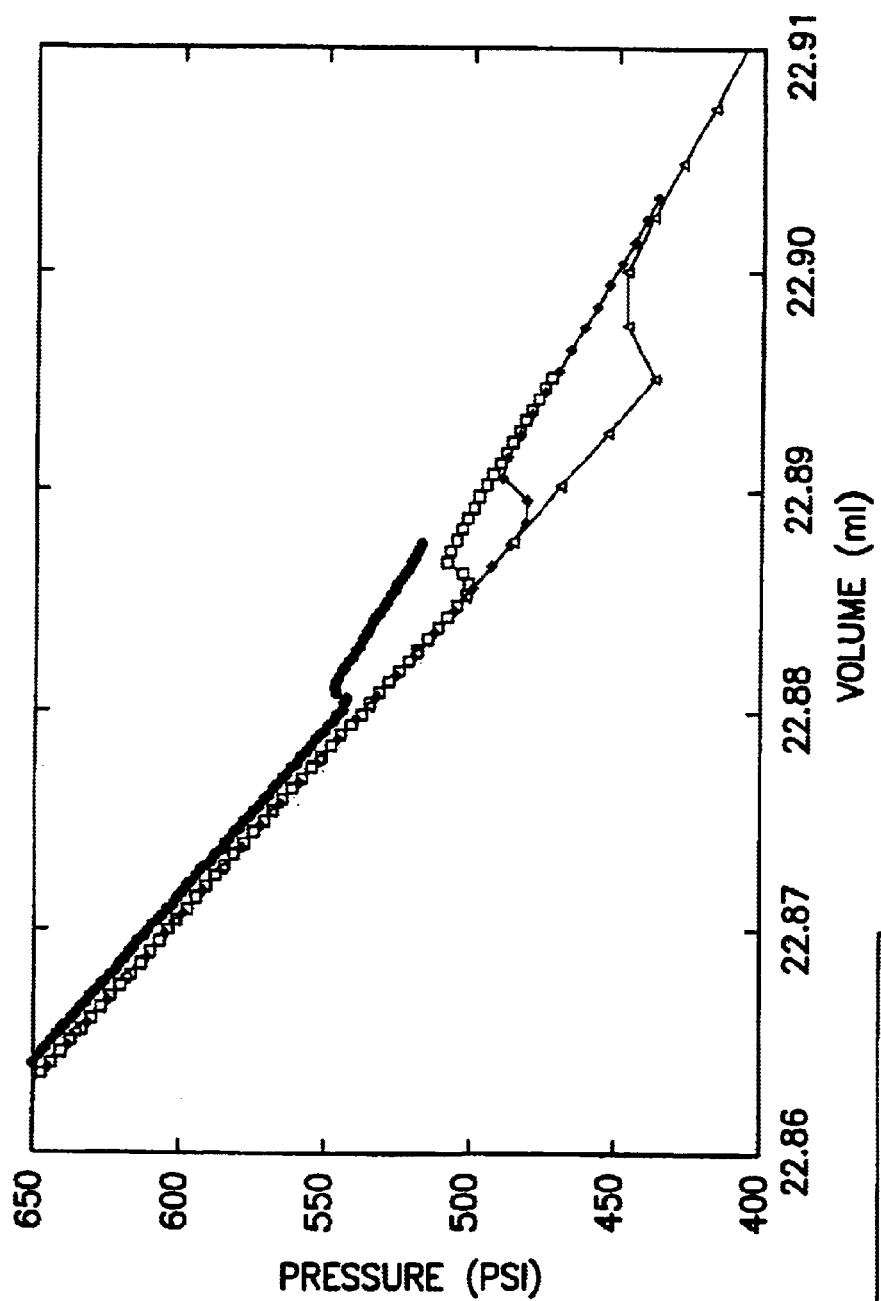
FIG. 8 is a graphical representation of the pressure versus volume characteristic of nitrogen dissolved in water as developed using a coaxial cylinder cell to induce cavitation wherein power is modulated between 0.1 W and 1 W and the depressurization rate is varied.
Figure 9:
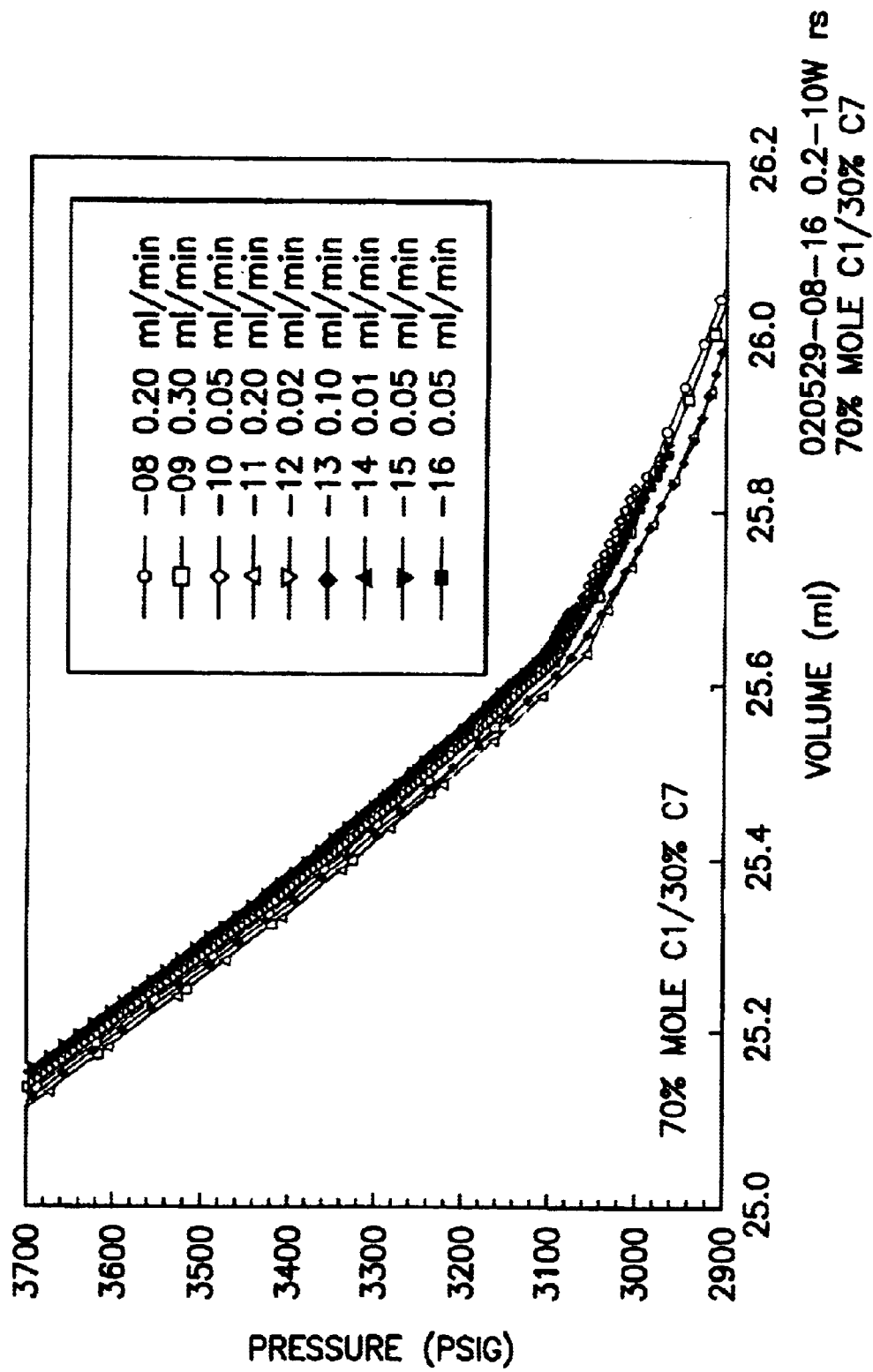
FIG. 9 is a graphical representation of a sample showing a compressibility indication of the presence of bubbles (no supersaturation).

A second acoustic source, a coaxial cylinder cell (such as that disclosed in commonly owned pending U.S. Ser. No. 10/167,516 to Liang filed Jun. 12, 2002) was also tested. The coaxial cylinder cell was used with a model flowline to test the cavitation technique. Both the total system volume and the volume exposed to acoustic energy are much smaller relative to the piston transducer apparatus. FIGS. 8 and 9 show the effects of depressurization rate and power on the pressure versus volume graph. The apparent compressibility was similar in the single-phase and two-phase regions. This may be due to the small amount of gas that evolved below the bubble pressure. This difference aside, the results (discussed below) are similar to those found using the piston transducer.

FIG. 8 shows data using a sample wherein nitrogen was dissolved in water. A coaxial cylinder was used to induce cavitation. The maximum power applied to the ultrasonic source was 1 W with 0.1 W applied between pulses. The depressurization rate varied between $\Delta V/V$ equal to $22 \times 10^{-6}$/min and $220 \times 10^{-6}$/min. The bubble point is approximately 565 psig. Like the example using the piston transducer, this data shows that slow depressurization minimizes supersaturation.

FIG. 9 is a graphical representation of a sample with no bubble supersaturation. In this sample, the compressibility change and the changes in electrical properties of the ultrasonic source, clearly coincide with the onset of bubble formation and no extrapolation is required. Thus, a measurement of the bubble point pressure may be made at the first onset of bubbles.

Figure 10:
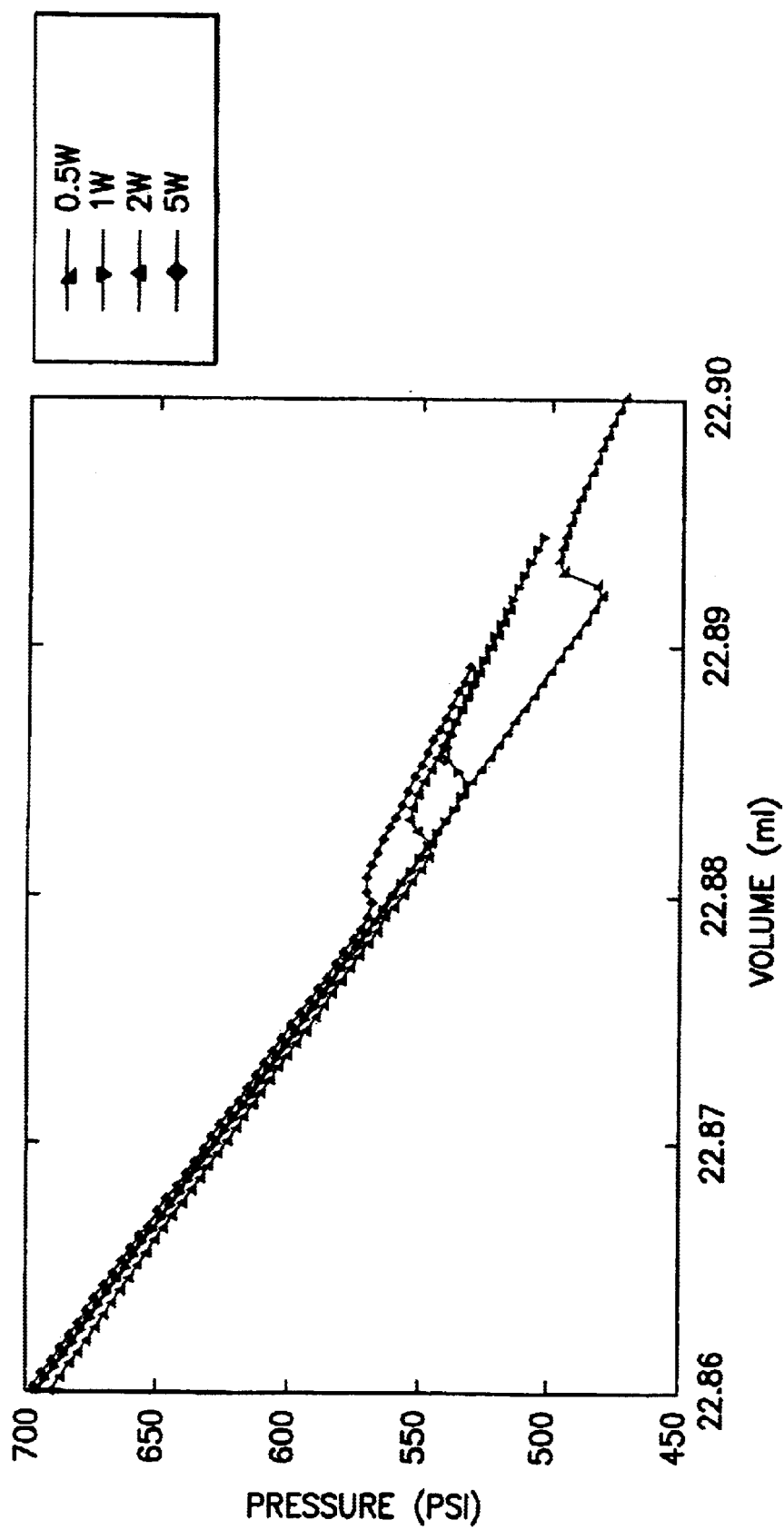
FIG. 10 is a graphical representation of the pressure versus volume characteristic of nitrogen dissolved in water as developed using a coaxial cylinder cell to induce cavitation wherein power is modulated between 0.5 W and 5 W.

FIG. 10 shows data using a sample wherein nitrogen was dissolved in water. A coaxial cylinder was used to induce cavitation. In this case, the maximum power applied to the ultrasonic cylinder varied between 0.5 W and 5 W with 0.1 W applied between pulses. The depressurization rate $\Delta V/V$ was equal to $44 \times 10^{-6}$/min. The bubble point was determined to be approximately 565 psig. Like the example using the piston transducer, this data shows that high power minimizes supersaturation.

Liquids typically have low compressibility (on the order of magnitude of about $10^{-4}$/bar). The compressibility of light gases, such as methane, is approximately equal to the inverse of the pressure. For example, at 100 bar pressure, the gas compressibility is about $10^{-2}$/bar; likewise, at 1000 bar the compressibility is about $10^{-3}$/bar. Thus, gases typically are roughly ten to a hundred times more compressible than liquids in borehole conditions (which can reach up to about 20,000 psi or about 1400 bar).

It should be kept in mind that the compressibility of a two-phase mixture is the volumetrically weighted averages of the compressibilities of all the phases. Thus, even at low pressure, the chance in compressibility at the bubble point is much less than if all the liquid had converted to gas. At high pressure there may be only a very small change of compressibility at the bubble point.

The observed compressibility below the bubble point was, in one sample measured, 1/100 of that predicted by thermodynamics under the assumption that the entire sample is in equilibrium. This is because most of the volume is not in thermodynamic equilibrium. The zero power results show that bubbles are very slow to form in the absence of a cavitation source, even at pressures considerably below the bubble point. Nonequilibrium depressurization will occur everywhere but in the immediate vicinity of the ultrasonic transducer.

In this example, only about 1% of the total volume was bubbly liquid. (The volume of free gas is considerably less than this.) In the piston cell, the volume was 148 cm$^3$. Thus the bubble-affected volume was about 1 cm$^3$, corresponding to the volume in proximity to the 1 cm diameter ultrasonic transducer.

It is significant that the slope of the P-V curve below the bubble point appears to be independent of both decompression rate and ultrasonic power. This is evidence that the sound field is merely a catalyst of bubble creation in a small, fixed volume.

The quantitative measurement of compressibility even in the single-phase regimes is subject to a number of pitfalls. For example, compressibilities derived from data presented above do not consistently agree with published data primarily because the apparatus used has certain compliant members (such as O-rings, tubing, and pressure-measuring diaphragms) that may compromise the accuracy of the compressibility measurement. These limitations may be readily overcome using a cell designed specifically to measure compressibility.

Figure 11:
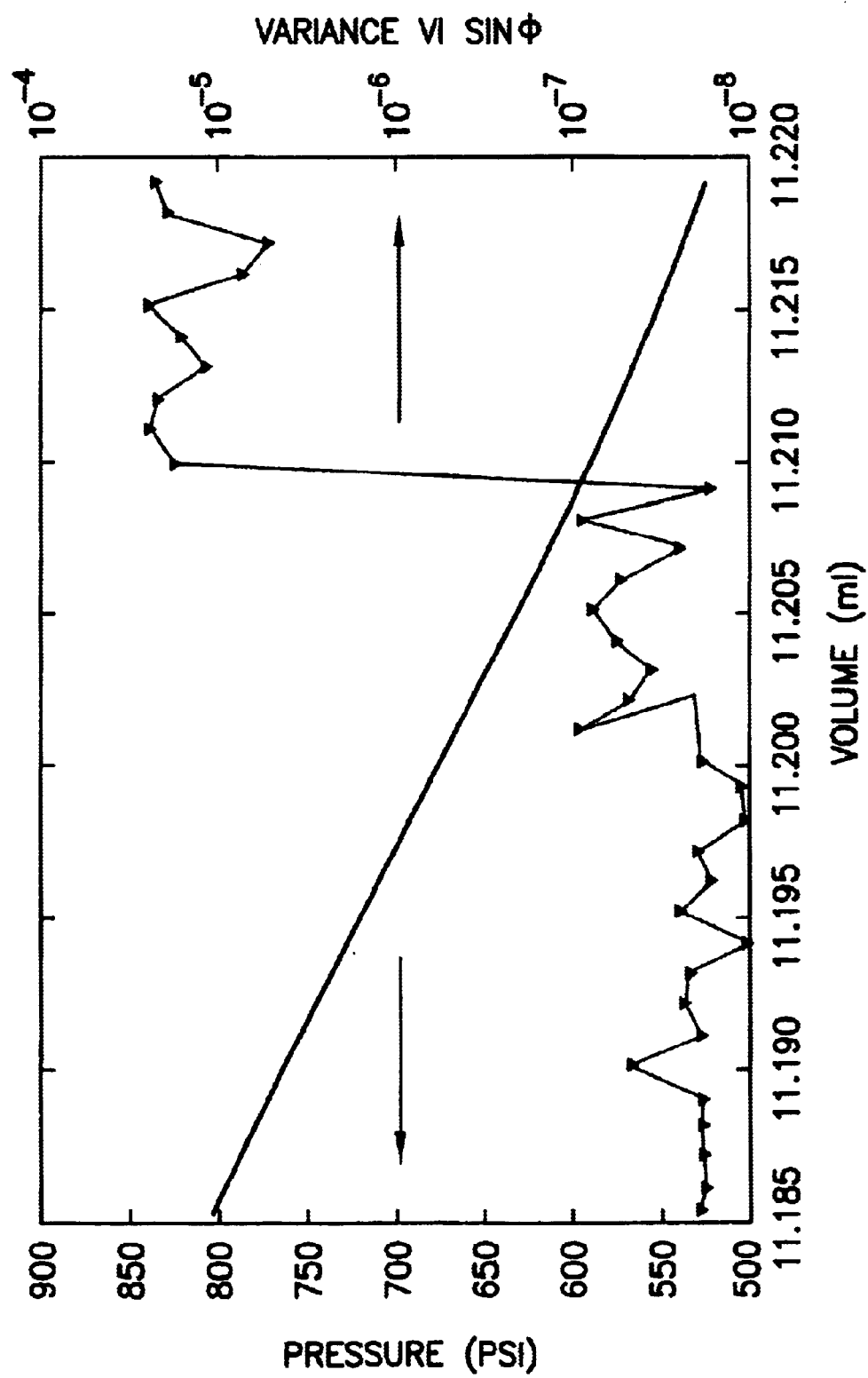
FIG. 11 is a graphical representation of the pressure versus volume characteristic of nitrogen dissolved in water as developed using a coaxial cylinder cell showing a change in the variance of V·I·sin $\phi$.

Often, pressure versus volume data is adequate to determine the bubble point. However, laboratory experience has shown that this technique is not infallible. FIG. 11 is a P-V curve of an example where the change in compressibility at the bubble point is very subtle. The data of FIG. 11 is from a sample of nitrogen dissolved in water wherein cavitation is induced using a coaxial cylindrical cell. The change in slope of this pressure-volume curve at the bubble point (595 psig) is nearly undetectable. However, the variance of an electrical parameter (discussed in more detail below), $V \cdot I \cdot \sin \phi$, where $\phi$ is the phase angle between the voltage (V) and the current (I), changes by several orders of magnitude at that point. Accordingly, in accordance with the present invention, when measurement of bubble point via the slope change of the pressure versus volume curve is impossible, the bubble point can be determined by purely electrical means.

Bubble and Gas Detection

The present invention further allows for gas detection in a sample by monitoring the compressibility of the sample, acoustic properties of the sample or electrical properties of the acoustic transducer. This method of bubble/gas detection may be performed with or without first nucleating the sample. Accordingly, the sample may be screened for the presence of gas. Such information is useful in itself or may be used to determine if a valid sample is obtained for bubble point determination. For example, if no gas is present in the sample (e.g. the sample is above the bubble point), the sample may be cavitated to nucleate bubbles and determine the bubble point. Alternatively, if gas is present, then the sample is below the bubble point.

In accordance with the present invention, bubbles of gases can be readily detected by monitoring acoustic properties and/or electrical properties. The presence of bubbles changes both the speed of sound and the density of the liquid. Thus, there is a sudden change in the radiation efficiency of the transducer when bubbles are produced. Because the radiation efficiency of an ultrasonic source is extremely sensitive to the presence of bubbles, bubbles may be produced and sensed at the same time with high reliability by measuring changes in the ultrasonic source's electrical properties. Various environmental conditions, such as temperature and pressure changes, can also cause the source's acoustic and electrical properties to vary. In the absence of bubbles, the acoustic and electrical properties of the transducer vary slowly, if at all. On the other hand, when bubbles are formed by cavitation, they can rapidly collapse, vibrate, or move. Any of these bubble motions also affects the sound field of the transducer (see the discussion of harmonics and subharmonics below) as well as the electrical properties of the ultrasonic source. Accordingly, unambiguous indicators of the presence of bubbles further include the fluctuation of radiation efficiency, and, therefore, fluctuation of one or more electrical properties.

Figure 12:
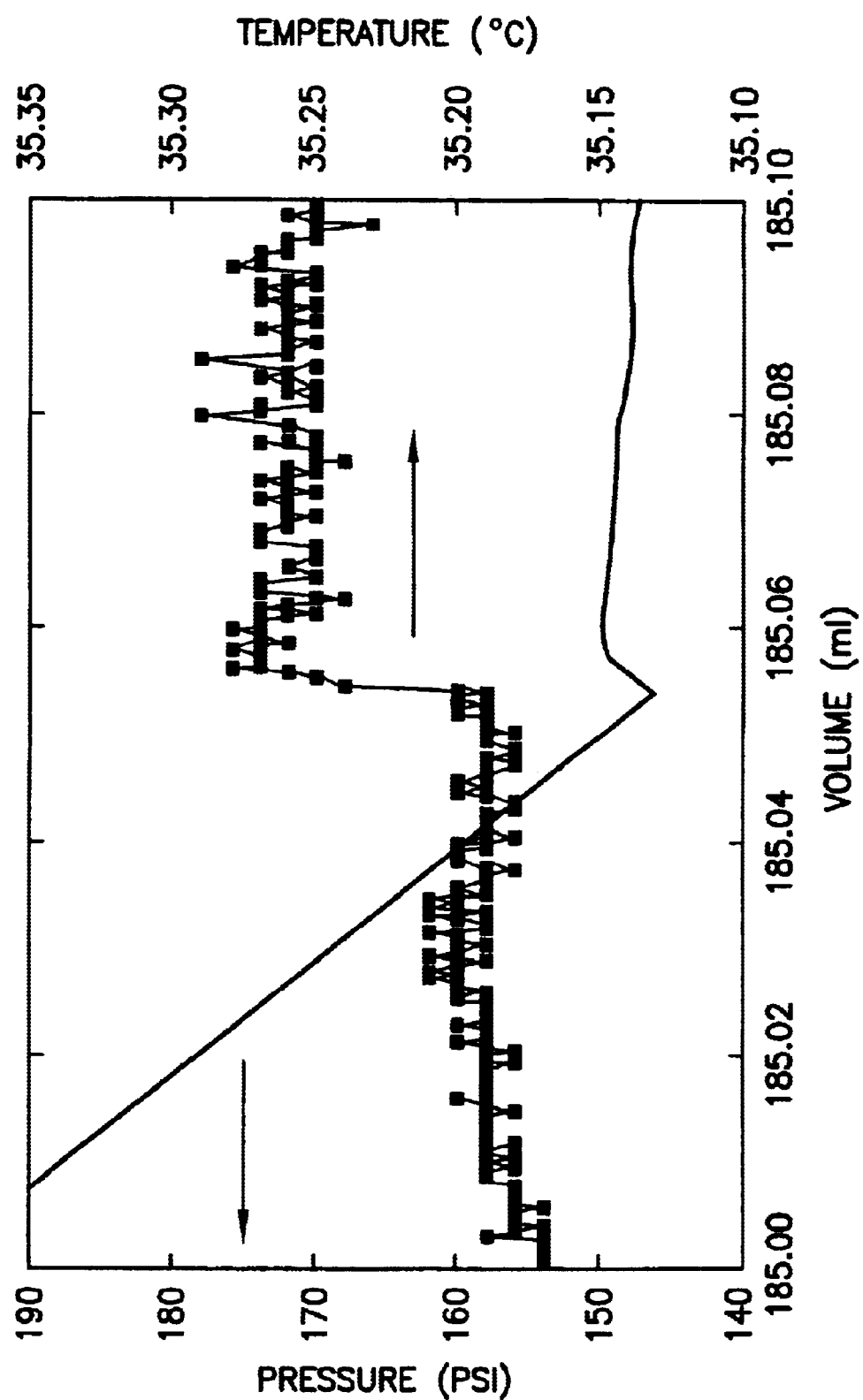
FIG. 12 is a graphical representation of the pressure versus volume of a nitrogen-water mixture as developed using a piston transducer showing a change in temperature.

It is commonly known that boiling is the most efficient way to transfer heat from a solid to a liquid. Thus, if there is a source of heat in contact with the liquid, the temperature of the liquid will increase suddenly at the bubble point. The source of heat can be the ultrasonic source that is used to induce cavitation. Furthermore. cavitation is also a way of transferring thermal energy to the sample; acoustic energy can be converted to thermal energy through the cavitation phenomenon. Temperature changes may be readily detected with a thermocouple or other temperature measuring device placed in contact with the fluid. An example of this detection technique is shown in FIG. 12. A continuous power of 0.5 W generated from a piston transducer was used to cavitate bubbles in a sample wherein nitrogen is dissolved in water. A small but distinct increase of the liquid temperature (about 0.08° C. in this sample) was coincident with the visible appearance of bubbles and slope change of the P-V curve. Accordingly, temperature changes and heat transfer rate changes are good indicators of the presence of bubbles.

Another indicator of the presence of bubbles is the generation of harmonics and subharmonics. Liquids and solids are linear elastic media. When sound is transmitted through them, speed, wavelength and amplitude may be altered, but the wave frequency is not. However, bubbles are nonlinear elements. When they are excited by an acoustic wave at a particular frequency, their motions can generate acoustic waves at a different frequency. Thus, a change in the appearance of harmonics is an indicator of bubbles.

Figure 13:
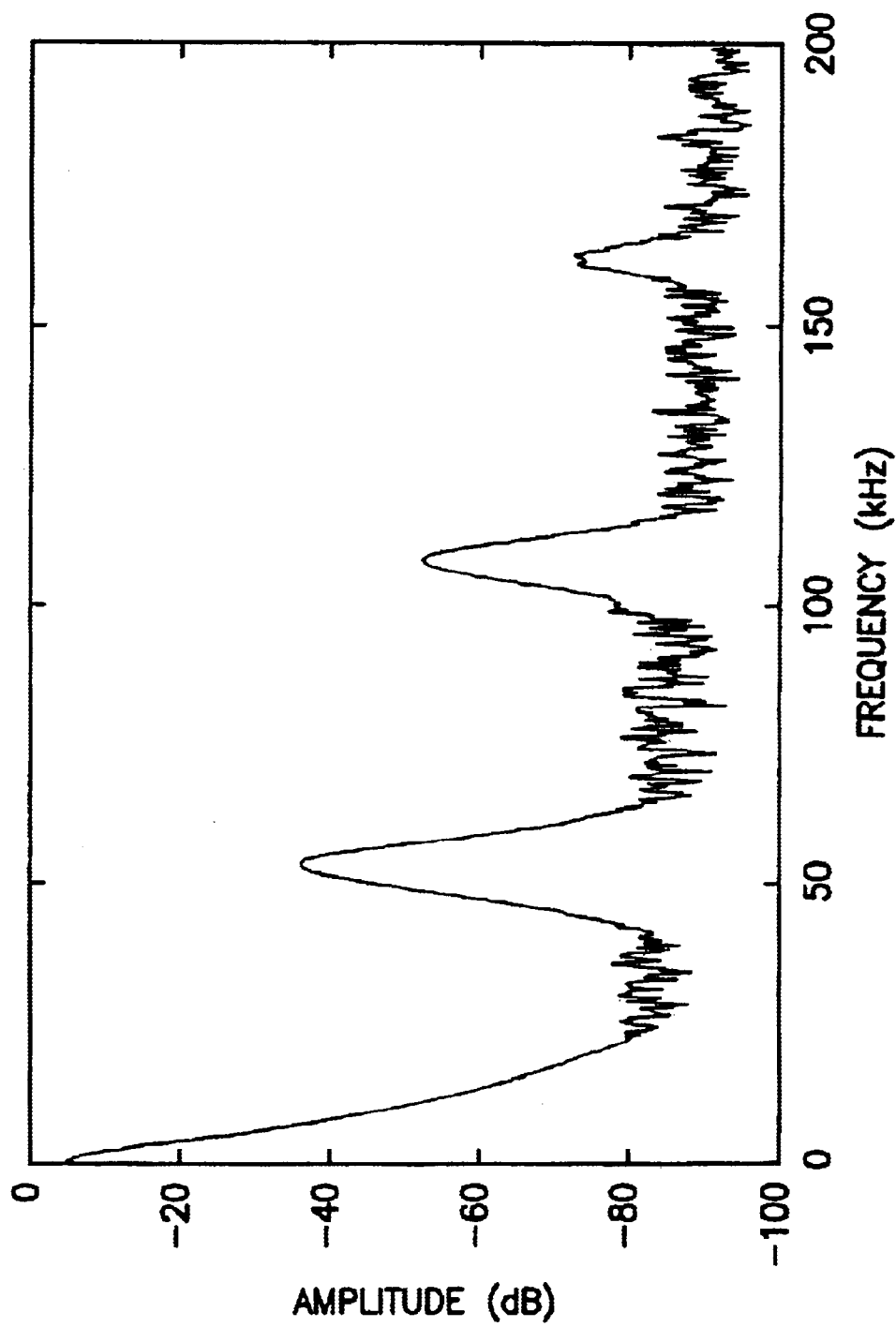
FIG. 13 is a graphical representation of a spectrum of a continuous wave signal at a receiver clamped to the outside of a pressure vessel.

A cell having a 1 cm diameter piston transducer operating in continuous wave mode at 53 kHz was used to cavitate gas bubbles at or near the bubble point pressure. A broadband receiver connected to a spectrum analyzer was secured to the outside of the cell with a clamp, and grease was used to ensure good acoustic coupling. A video camera inside the cell was used to monitor bubble production to correlate laboratory data with bubble formation. At pressures above the bubble point, the receiver detected sound only at 53 kHz. However, when bubbles were present, many overtones were detected as shown in FIG. 13.

The presence of gas bubbles in a liquid has a large effect on both the speed and attenuation of sound. Thus, acoustic radiation of the cavitating transducer may be sensed by a second transducer acting as a receiver. In the presence of bubbles, the transit time will increase and the received amplitude will decrease.

In accordance with the present invention, even tiny and/or transient bubbles affect large fluctuations of transducer electrical properties, such as resonance frequency, voltage, voltage squared, current, current squared, phase angle between current and voltage, power dissipation, electrical impedance, or combinations thereof. The parameter monitored will depend on the design of the driver circuit and is not necessarily electrical impedance. This list is not intended to be limiting; additional indicators not listed above may also be used depending on the design of the driver circuit.

In a further embodiment, the voltage across the transducer is monitored and applied to a squaring circuit. A demodulator and digitizer are used to record the voltage squared ($V^2$) as a function of time during the high power pulse. In another embodiment, the electrical parameter V·I·sin φ is monitored during the pulse, as above, φ is the phase angle between the voltage, V, and the current, I. Note that in this embodiment, no time-delayed acoustic waveform will be detected.

This technique was applied to a mixture of methane and n-heptane in a model flowline apparatus surrounded by a coaxial-cylinder type ultrasonic resonator. The time record of $V^2$ in the single-phase region is the flat line (A) shown in FIG. 14. After the pressure was lowered and bubbles produced, the voltage increased as shown by the noisy line (B). The increase was due to a change in the transducer's acoustic radiation efficiency and represents bubble formation.

Figure 14:
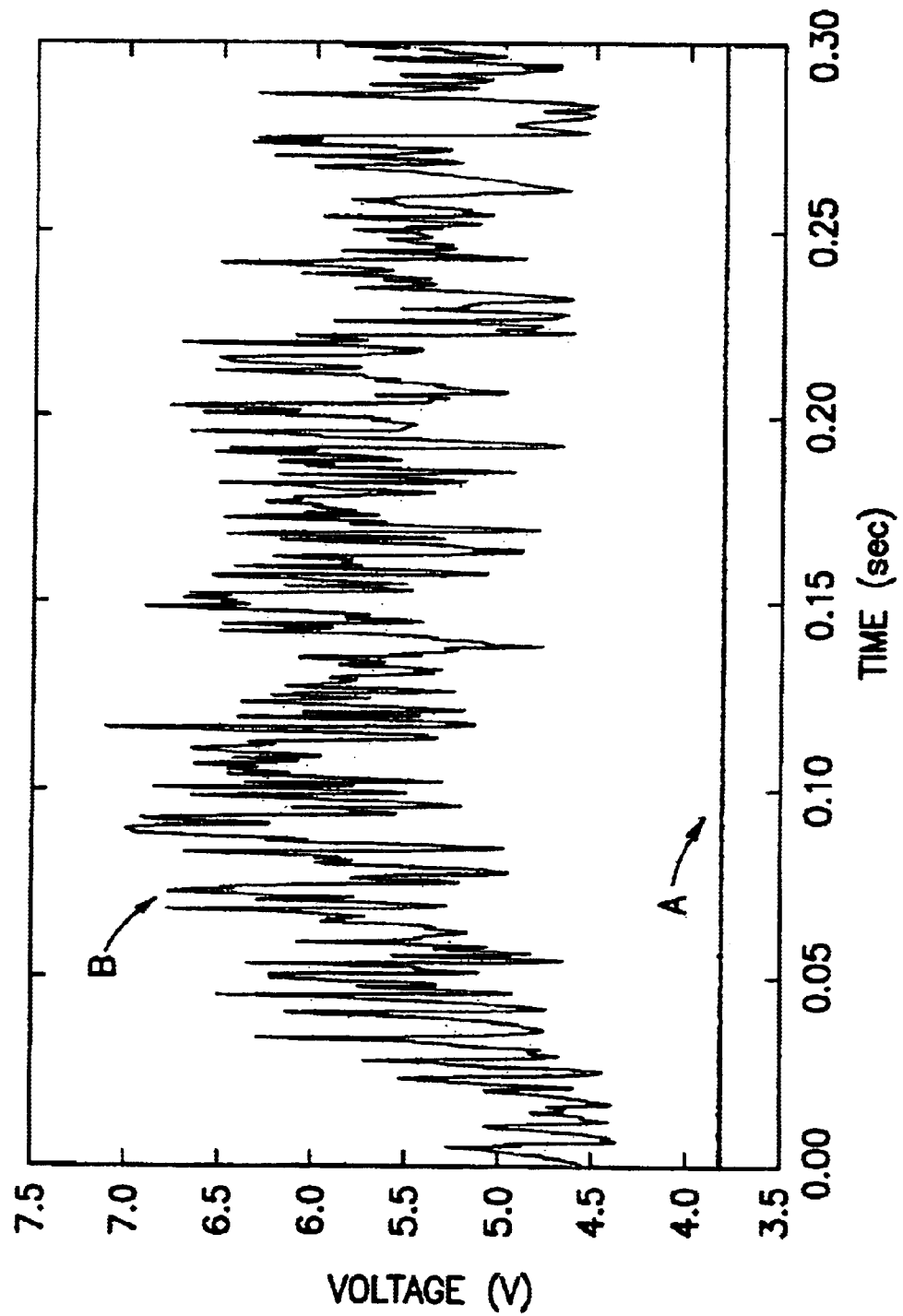
FIG. 14 is a graphical representation showing the demodulated voltage across the ultrasonic transducer when bubbles are present and when bubbles are not present.
Figure 15:
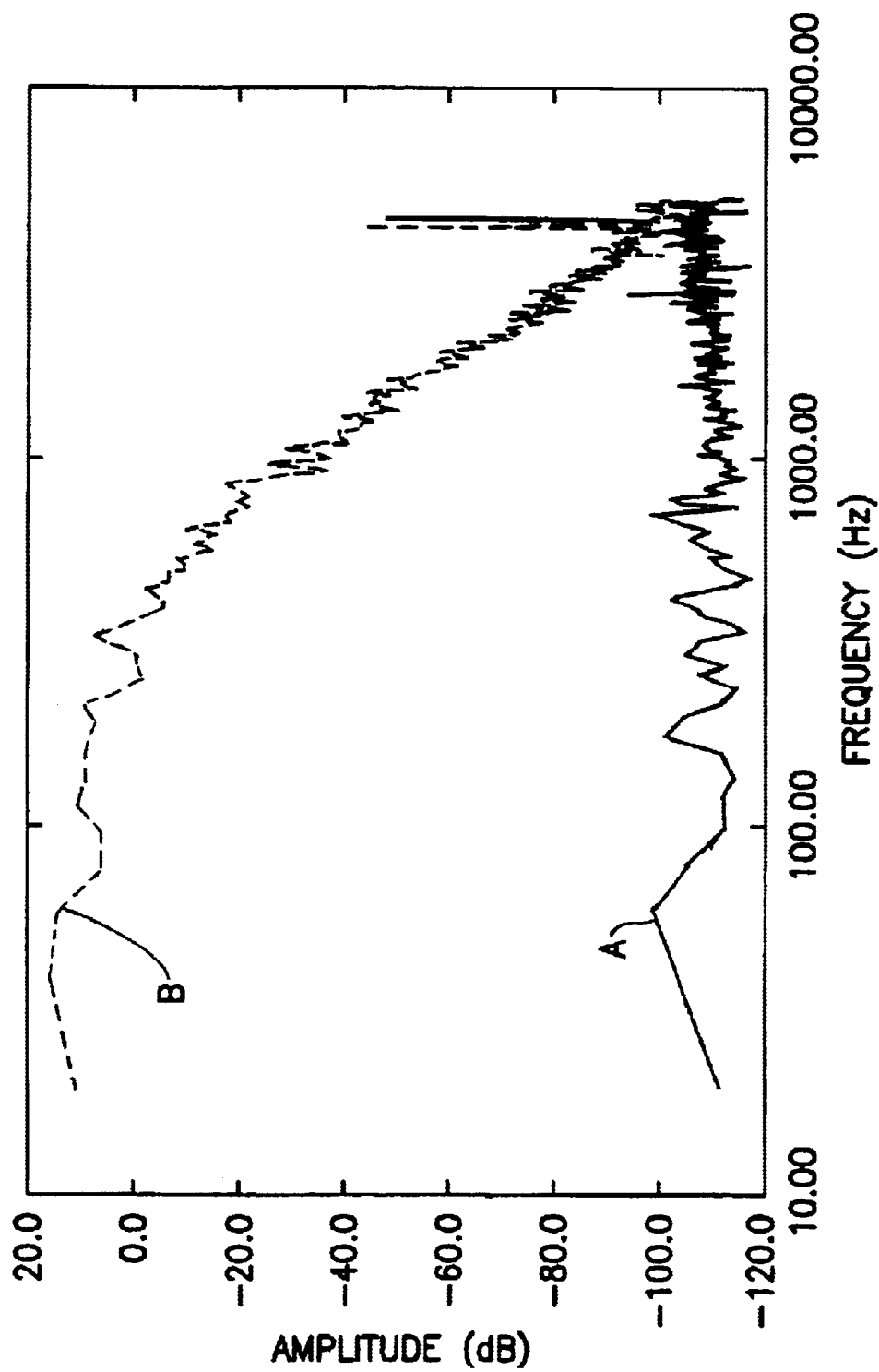
FIG. 15 is a graphical representation of a Fourier transform of the data shown in FIG. 14.

The frequency spectrum of the fluctuations gives insight into the processes by which bubbles affect the electrical properties of an acoustic transducer. The Fourier transforms of the time records of FIG. 14 are shown in FIG. 15. As shown in FIG. 14, when no bubbles are present near the transducer, the squared and demodulated voltage across the ultrasonic transducer is quiet during a high pulse power (line A). In the presence of bubbles $V^2$ is both higher and erratic (line B). FIG. 15 shows that above the bubble point, the frequency spectrum is flat and reflects the noise floor of the measurement. Below the bubble point, the spectrum has high power at low frequency and drops rapidly above about 500 Hz. This suggests that fluctuating bubble processes are occurring on a time scale of milliseconds.

Monitoring the variance of fluctuations in accordance with the present invention is a sensitive method of detecting bubble presence. As shown in previously discussed FIG. 11, this method was used to reliably detect gas bubbles when other techniques failed. Note that the variance of V·I·sin φ suddenly changes by many orders of magnitude at the onset of bubble formation.

Figure 16:
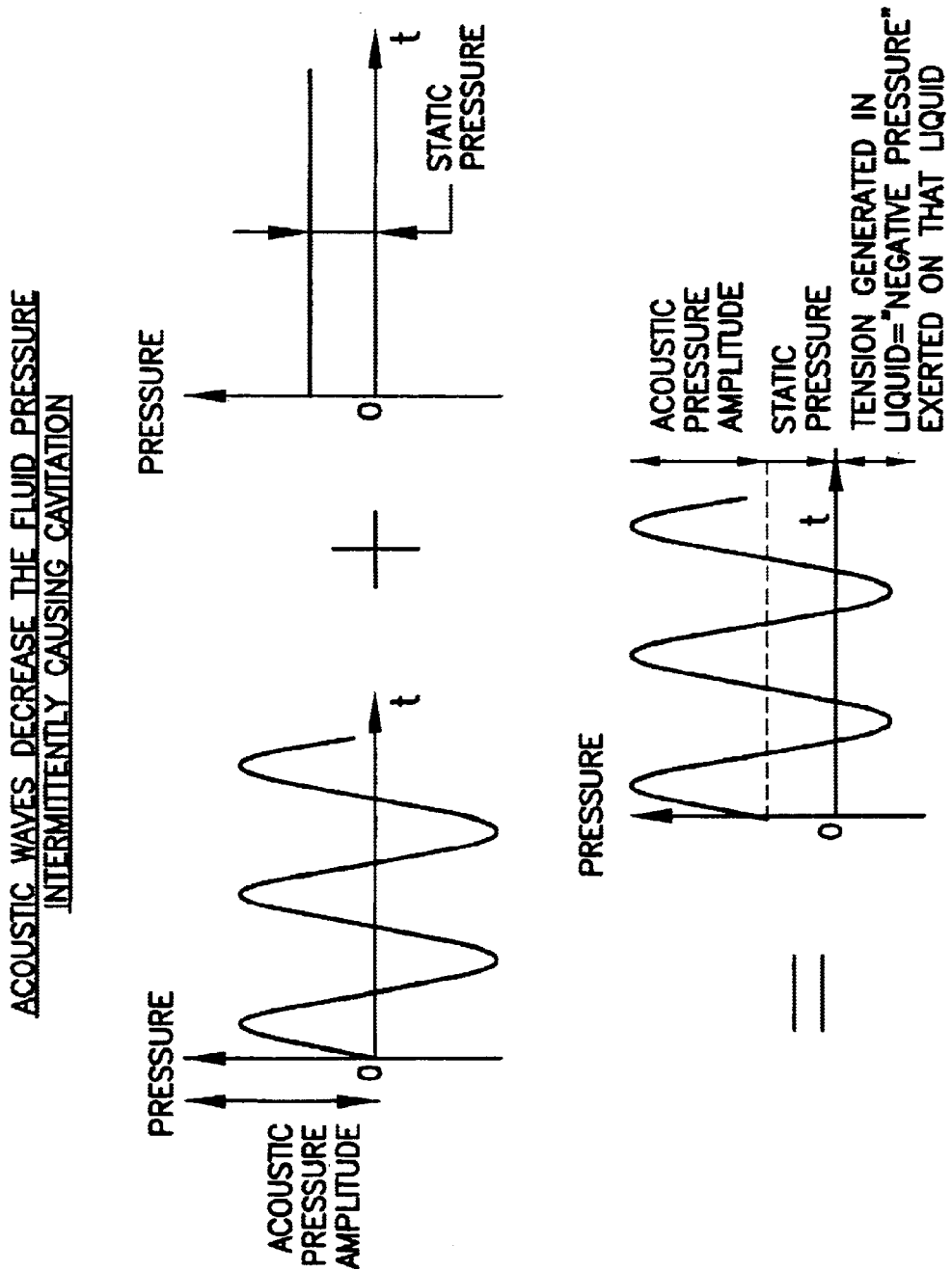
FIG. 16 is a schematic showing the mechanism of bubble generation by sound waves at a static pressure substantially above the bubble point.
Figure 17:
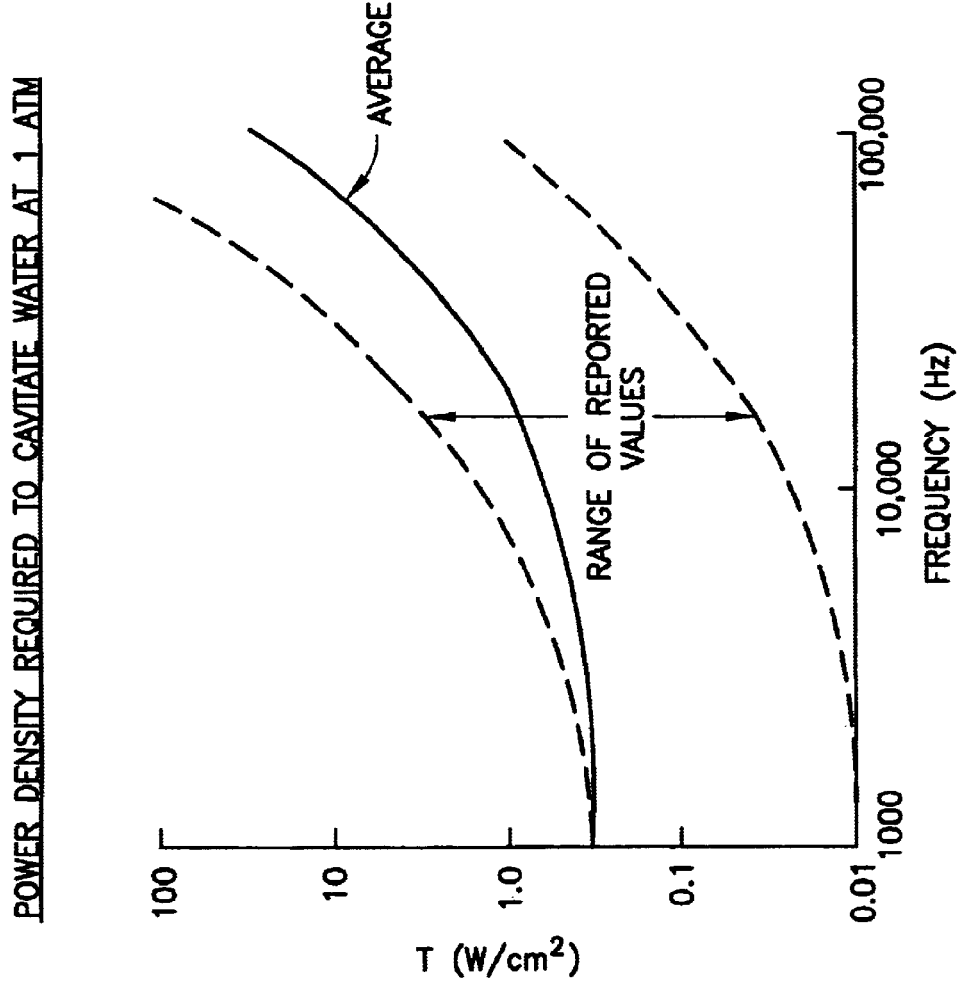
FIG. 17 is a graphical representation of the frequency dependence of cavitation efficiency of acoustic transducers.

Acoustic methods can be used to estimate bubble point even when the ambient pressure is somewhat above the anticipated bubble point pressure. When the sound pressure level is increased, the peak-to-peak variation of pressure is increased. When the pressure in the rarefaction half-cycle dips below the bubble pressure, transient cavitation can occur, as shown in FIG. 16. The rarefaction pressure is related to the transducer power by $$W = \frac{p^2 AF}{2\rho c E} \tag{1}$$

where:
W=electrical power supplied to the transducer (watts)
p=sound pressure (N/m$^2$)
A=area of the transducer face in the piston model (m$^2$)
ρ=fluid density (kg/m$^3$) (for water this term equals 1000)
c=fluid speed of sound (m/s) (for water this term equals 1500)
E=transducer efficiency
F=frequency factor The frequency factor accounts for the reduced cavitation at high frequency as shown in FIG. 17. Below 10 kHz, it is approximately unity.

Figure 18:
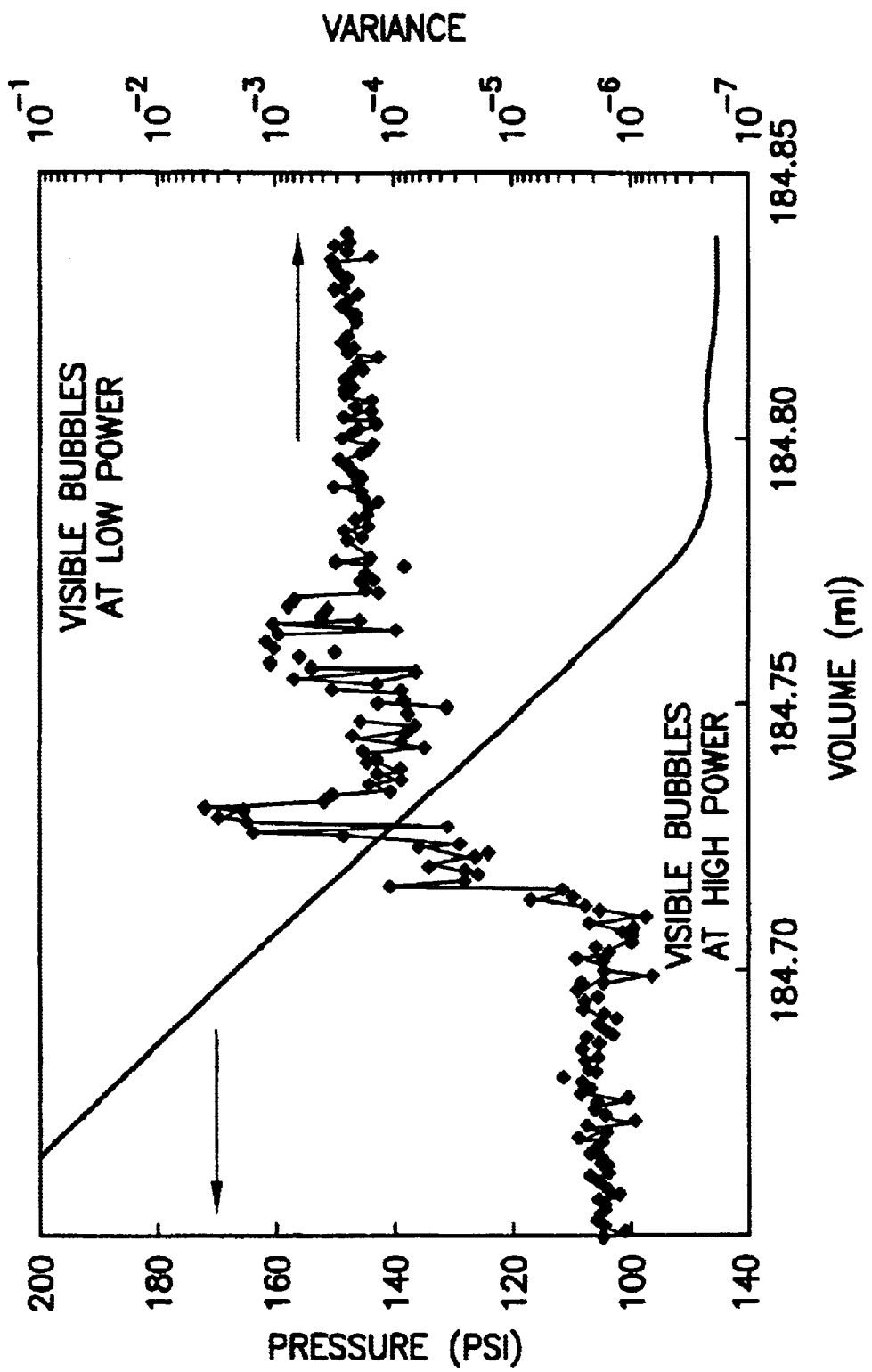
FIG. 18 is a graphical representation of the cavitation of nitrogen dissolved in water wherein cavitation occurs at a pressure substantially above the bubble point.

FIG. 18 shows that cavitation can be induced even when the ambient pressure is well above the bubble pressure. The piston transducer operating at 53 kHz had a diameter of 1 cm. an efficiency of 0.9 and a frequency factor of about 10. The fluid sample was nitrogen dissolved in water. The transducer power alternated between 0.5 W and 30 W (i.e. 0.5 W of continuous wave energy was applied between the 30 W pulses). Bubble creation was monitored by video camera and by measuring the variance of an electrical characteristic of a piston transducer operating at 53 kHz during both high power and low power intervals.

At a higher power, the first indication of bubble occurred at 150 psig, about 65 psi above the bubble point for this solution. The variance measure increased by several orders of magnitude. The video observations suggested that the bubbles were transient, appearing only when high power was radiated by the transducer. At the lower power, the first indication of bubbles occurred at about 10 psi above the bubble point. Accordingly, bubbles may be nucleated by holding the static pressure constant while increasing the acoustic pressure applied to the sample.

The pressure of first appearance of bubbles approximately follows the expected power dependence. FIG. 19 shows that as power increases, bubbles are seen (visually and electrically) at higher ambient pressures. This data is in agreement with the theory with no adjustable parameters. Thus, the true bubble pressure, 88 psig in this case, can be estimated from a single measurement at elevated power with knowledge of the transducer characteristics.

Gas detection is of greatest value when the fluid sampling tool is extracting fluid from the earth formation. Therefore, the gas detector should preferably operate while liquid is flowing at high speeds, such as up to 100 cm/s. For example, Schlumberger's MDT tool uses a 5 mm inner diameter flowline through which fluid may now at 100 cm/s. If the acoustic transducer is sensitive to the fluid in the line over a length of 3 cm, the detection should occur within 0.03 sec. This is about ten times longer than the duration of bubble motions that cause the electrical fluctuations described above. Coaxial cylindrical transducers are also suitable for gas detection because sound energy may be focused in the liquid without obstructing or diverting the flow.

If the ambient pressure is far above the bubble point, if a determination of maximum accuracy is required, or if compressibility information is required, it is desirable to capture a stationary sample. This sample can be routed to a sidetrack, while flow continues through a bypass line. This sidetrack is equipped with valves to temporarily isolate it from the flowline, an expansion device such as a piston, and a pressure gauge. The expansion device does not require a large volume. The compressibility of most single-phase liquids is on the order of magnitude of $10^{-4}$/bar. Thus, to reduce the pressure of the liquid by 100 bar (1500 psi), an expansion of 1% is required.

The speed of bubble point measurements may be improved by depressurizing the sample two or more times. The first time, depressurization can be done quickly for a rough estimate of bubble pressure. A second slower depressurization over the pressure range in the vicinity of the bubble point will result in a more accurate determination of the bubble point. It has been found that once bubbles come out of solution, it takes several hours to redissolve them, even at pressures far above the bubble point. Therefore, once bubbles have been produced, it is preferable to replace the samples (and sweep away all bubbles) before a repeat determination is attempted.

Accordingly, one embodiment of the present invention relates to an enhanced method of determining phase characteristics of a formation fluid. Using this method, a first fluid sample is withdrawn from the formation fluid (such as by using a formation sampling tool, either captured volume or flowing). The first fluid sample is rapidly depressurized and the onset of bubble formation is detected. The sample pressure corresponding to the first onset of bubble formation is measured. Because the sample was rapidly depressurized, it is likely that the measured bubble point pressure is below the true bubble point. Accordingly, a second fluid sample is withdrawn and slowly depressurized over a range of pressures deduced from the results of the first depressurization. Sample pressure at the detection of the onset of bubble formation is measured. Preferably, the first fluid sample is purged prior to withdrawing a second fluid sample. Most preferably, the formation sampling tool is equipped with an ultrasonic source that is activated to assist in the nucleation of bubbles in both the first and second samples. In accordance with the method disclosed above, it is preferable to detect the onset of bubble formation by monitoring electrical properties of the ultrasonic source. Furthermore, the detection of harmonics or subharmonics or the detection of changes in temperature may be used to identify for the formation of bubbles in both samples.

For efficient operation, the natural frequency of vibration of the transducer and the frequency of the transmitter electronics should preferably coincide.

Figure 20A:
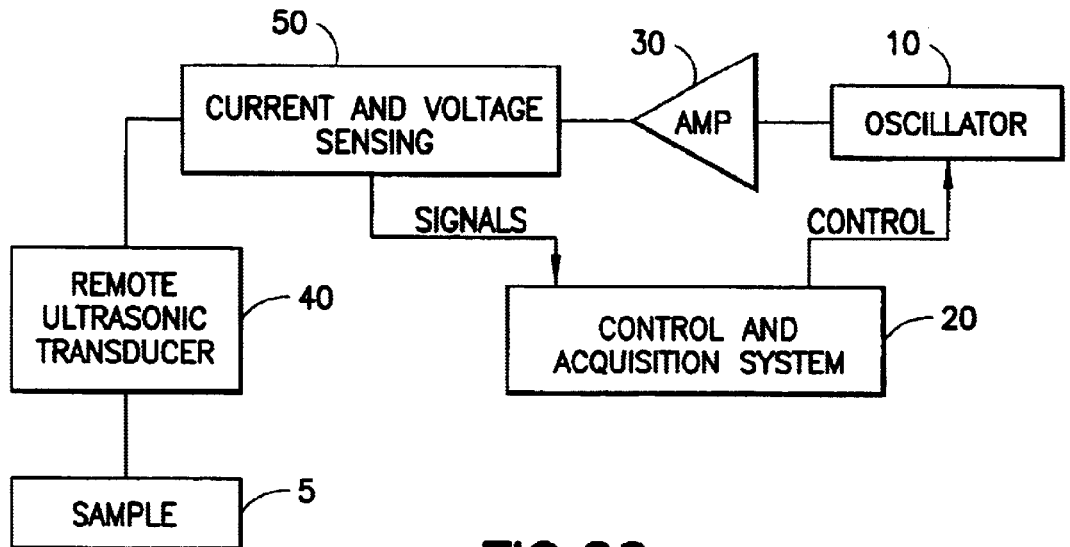
FIGS. 20a and 20b are block diagrams of the bubble detection scheme.
Figure 20B:
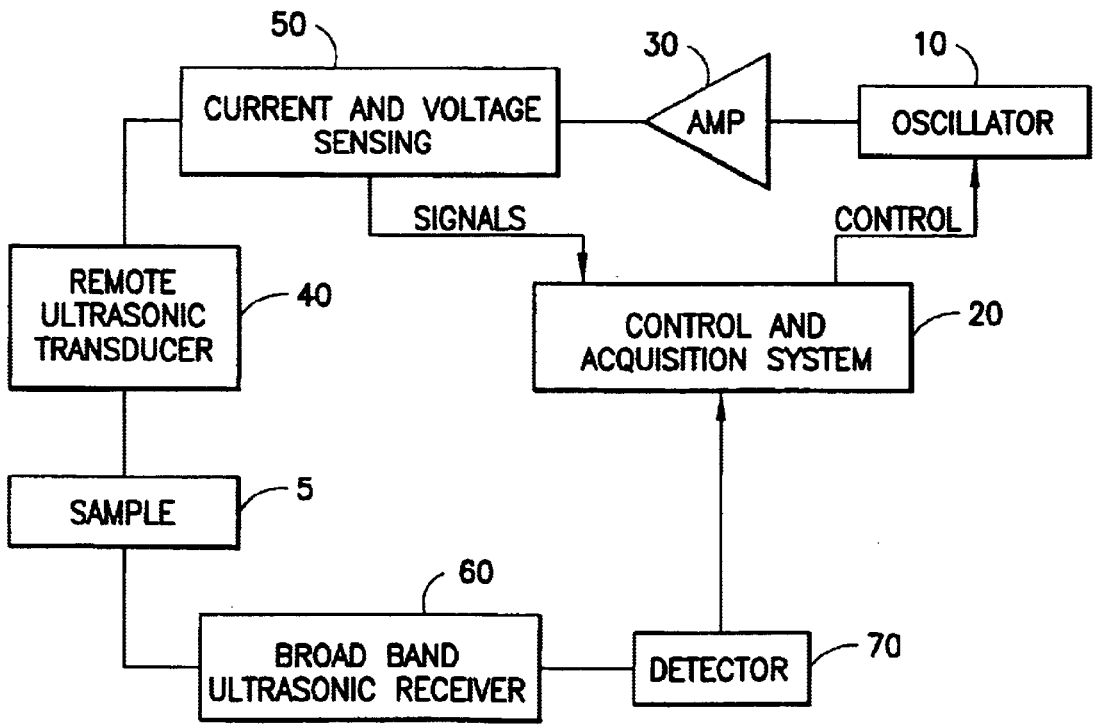

FIGS. 20a and 20b show block diagrams of systems for generating electrical drive, detecting a cavitation signal and stabilizing the power output of the ultrasonic transducer. For both of these diagrams, the time constant of the control loop (approximately 1 second) is long compared to the characteristic time of bubble-related fluctuations (around 0.001 seconds). The blocks in the diagrams suggest a certain division of functions but it will be known to those skilled in the art that these functions can be combined or divided in other ways.

As shown in FIG. 20a, an oscillator 10 operates at a variable frequency set by the control system 20. The oscillator 10 feeds an amplifier 30 to provide energy to drive the transducer 40. The signal to the transducer 40 can be a monochromatic continuous wave waveform of constant magnitude. In the presence of cavitation in the sample 5, bubbles form and collapse, thereby changing the radiation efficiency of the transducer 40 and modulating the amplifier output voltage and current. Voltage and current sensing circuits 50 monitor the feed line of the transducer. The transducer 40 operating frequency and electrical properties change with environmental and loading conditions. The voltage and current signals are fed to a data acquisition digitizer for processing. The control system 20 analyzes the phase of the signals and generates a feedback signal to drive the transducer at its resonant frequency. This maximizes the system's energy efficiency. Current and voltage are also used in feedback to maintain constant power to the transducer 40. This feature is important because (1) there is no direct way to measure the acoustic wave pressure at the face of the transducer and (2) varying power levels affect the onset of cavitation. A benefit of this system is its ability to both generate and detect cavitation with one transducer. In this embodiment, a feedback system is used to maintain the transducer at its resonance frequency and to ensure that its power output is constant. FIG. 20b is a block diagram of a system useful for the detection of bubbles based on appearance of, or change in, harmonics or subharmonics. This system includes the sampling means 5, the oscillator 10, the control system 20, the amp 30, the transducer 40, and the current/voltage sensing circuit 50 as described above with reference to FIG. 20a. However, this embodiment further includes a receiver 60 and a detector 70 that communicates with the control system 20.

Digital processing can be used to extract the components of in-phase and out-of-phase current and voltage. These components are used to compute the operating frequency and transmitted power of the transducer. Alternatively, the current and voltage signals can be processed with analog circuitry, for example with lock-in amplifiers. Both digital and analog control methods have been used successfully. The feedback system for the transducer operation preferably has a time constant larger than the fluctuation time. For example, a time constant of 1 second has been found to be useful.

The amplifier output voltage squared is one simple and useful parameter to detect and measure. The cavitation-induced modulation can be detected digitally by the acquisition system or with an appropriate analog demodulator. The feedback system is purposely too slow to null electrical variations in the kilohertz frequency range. In a properly designed system, the statistical variance of electrical measurements may increase by three orders of magnitude or more in the presence of bubbles.

If needed, to limit heating in the vicinity of the transducer, pulse mode operation can be used. The selection of pulse width and duty cycle is a compromise between heating and quantity of data that can be accumulated per unit time. High power sound pulses are, for example, 0.1 second long. At many times during this interval, one or more indicators or radiation efficiency are instantaneously detected and recorded. The statistical properties of each of these indicators are then computed digitally over the duration of one or more pulses. Low power is optionally applied to the transducer between high power pulses.

Figure 21A:
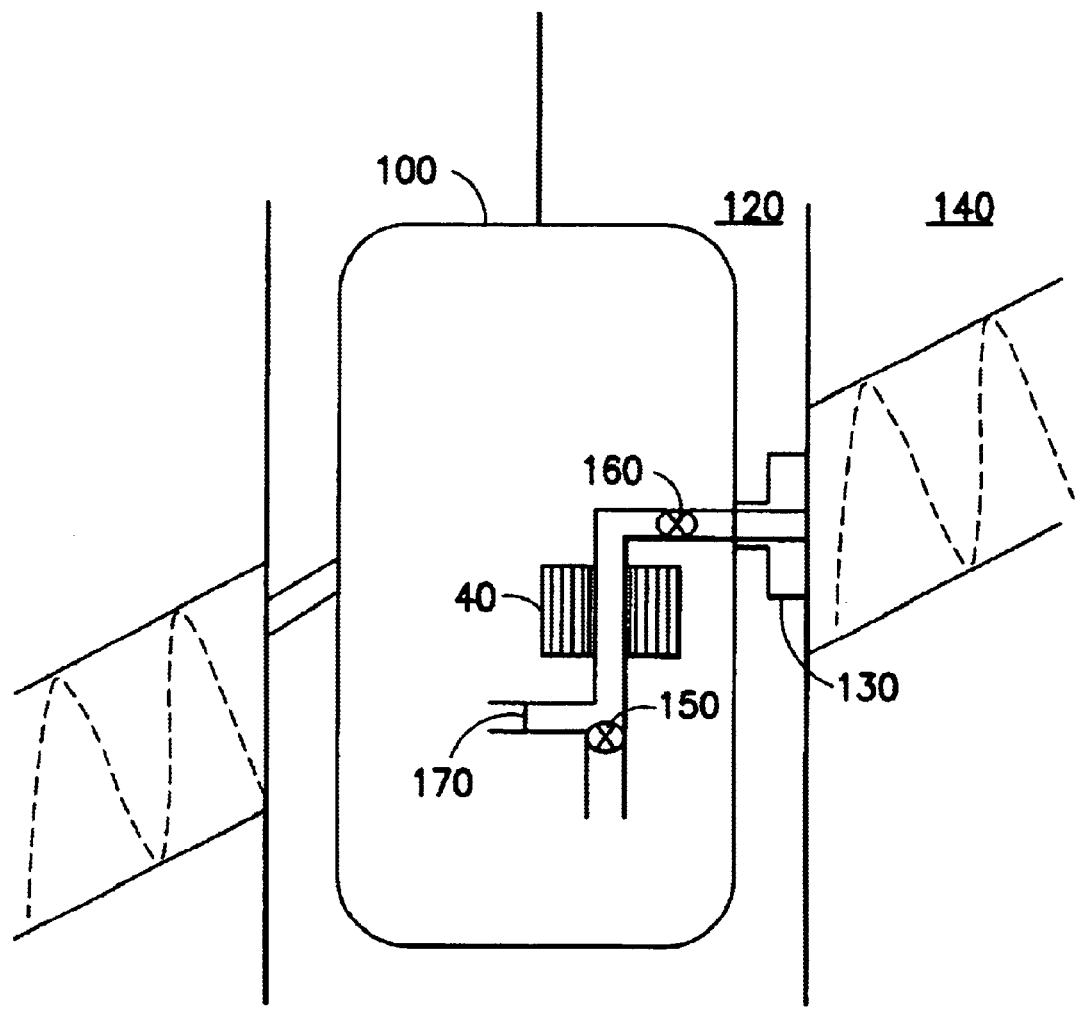
FIGS. 21a and 21b are schematics of sampling devices incorporating the present invention.
Figure 21B:
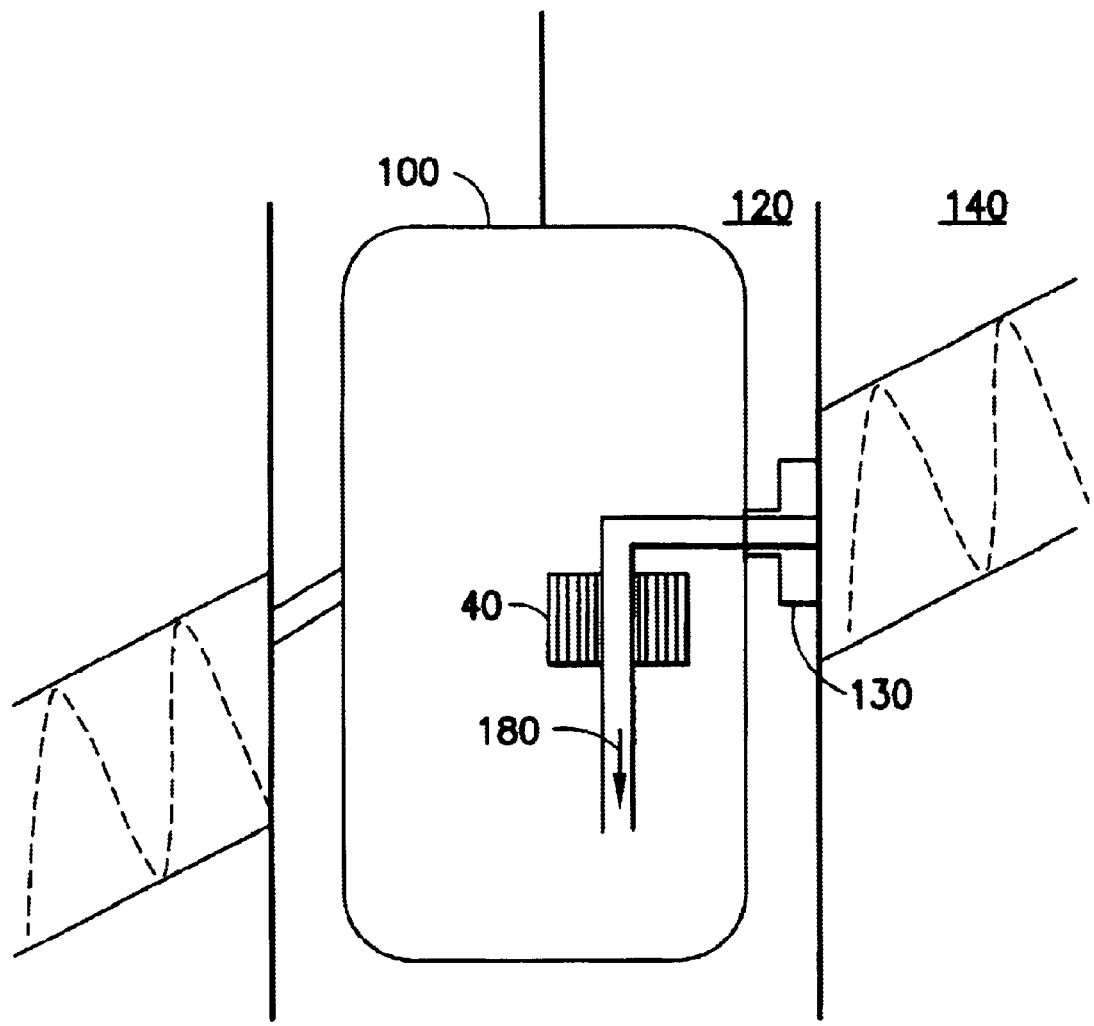

As indicated above, the present invention may be implemented in a tool string having a captured volume sampling means or a flowing sampling means. FIGS. 21a and 21b are schematic diagrams of a borehole apparatus useful in the present invention. In this non-limiting embodiment, the tool 100 equipped with an ultrasonic transducer 40 (in this case a cylindrical transducer) is suspended in the borehole 120. The sampling means 130 is used to obtain a formation fluid sample from the formation 140. FIG. 21a shows one embodiment wherein the sampling means obtained a captured or fixed volume sample. Valves 150 and 160 isolate a portion of the formation fluid. The sample is depressurized using the piston 170. Bubbles are cavitated and/or detected using the transducer 40. FIG. 21b shows another embodiment wherein the transducer 40 cavitates and/or detects bubbles in a sample flowing 180 through the transducer 40. One skilled in the art would recognize that other tools may be suitably adapted.

Furthermore, the present invention is not limited to borehole applications. It may be suitably employed in surface apparatus, PVT Laboratory settings and other bubble cavitation and identification applications wherein the sample under test is subject to the pressure and temperatures typical of borehole conditions (e.g. borehole-like conditions).

While the invention has been described herein with reference to certain examples and embodiments, it will be evident that various modifications and changes may be made to the embodiments described above without departing from the scope and spirit of the invention as set forth in the claims.

We claim:

1. A method of fluid analysis for determining phase characteristics of a formation fluid, comprising the steps:
   a. withdrawing a sample under borehole-like conditions;
   b. depressurizing said sample;
   c. nucleating bubble formation in said sample by activating an ultrasonic source in fluid communication with said sample; and
   d. detecting onset of bubble formation in said sample by monitoring the compressibility of said sample.

2. The method of claim 1, wherein said sample is a stationary sample.

3. The method of claim 1, wherein said sample is a flowing sample.

4. The method of claim 1, wherein said ultrasonic source is selected from the group consisting of a piston transducer and a coaxial cylinder cell.

5. The method of claim 1, further comprising: measuring the pressure of said sample at the onset of bubble formation, further comprises the steps of:
   a. developing a first pressure-volume function of said sample prior to bubble formation;
   b. developing a second pressure-volume function of said sample after bubble formation; and
   c. extrapolating the intersection of said first and second functions, wherein said intersection represents the bubble point pressure.

6. A method of fluid analysis for determining phase characteristics of a formation fluid, comprising the steps:
   a. withdrawing a sample under borehole-like conditions;
   b. depressurizing said sample;
   c. nucleating bubble formation in said sample by activating an ultrasonic source in fluid communication with said sample; and
   d. detecting onset of bubble formation in said sample by monitoring the temperature of said sample.

7. The method of claim 6, further comprising supplying thermal energy to said formation fluid sample.

8. A method of fluid analysis for determining phase characteristics of a formation fluid, comprising the steps:
   a. withdrawing a sample under borehole-like conditions;
   b. depressurizing said sample;
   c. nucleating bubble formation in said sample by activating an ultrasonic source in fluid communication with said sample;
   d. detecting onset of bubble formation in said sample by monitoring one or more ultrasonic source properties; and
   e. measuring the pressure of said sample at the onset of bubble formation.

9. The method of claim 8, wherein said ultrasonic source properties is selected from a group consisting of resonance frequency, voltage, voltage squared, current, current squared, phase angle between current and voltage, power dissipation, and electrical impedance and combinations thereof.

10. A method of fluid analysis for determining phase characteristics of a formation fluid, comprising the steps:
    a. obtaining a sample under borehole-like conditions, wherein said sample is in fluid communication with an ultrasonic source;
    b. nucleating bubbles in said sample by activating said ultrasonic source;
    c. detecting the onset of bubble formation by measuring one or more ultrasonic source properties.

11. The method of claim 10, further comprising measuring the sample pressure at the onset of bubble formation.

12. The method of claim 10, wherein said sample is a stationary sample.

13. The method of claim 10, wherein said sample is a flowing sample.

14. The method of claim 10, wherein said ultrasonic source is selected from the group consisting of a piston transducer and a coaxial cylinder cell.

15. The method of claim 10, wherein the step of nucleating bubbles in said sample further comprises holding the static pressure of said sample constant while increasing the acoustic pressure applied to said sample.

16. The method of claim 10, wherein the step of nucleating bubbles in said sample further comprises depressurizing said sample.

17. The method of claim 16, wherein the step of depressurizing said sample is comprised of incrementally increasing the volume of said sample at a known rate.

18. The method of claim 17, further comprising allowing the pressure of said sample to equilibrate with each incremental change in volume.

19. The method of claim 10, wherein said ultrasonic source properties is selected from a group consisting of resonance frequency, voltage, voltage squared, current, current squared, phase angle between current and voltage, power dissipation, and electrical impedance and combinations thereof.

20. A method of fluid analysis for determining phase characteristics of a formation fluid, comprising the steps:
 a. obtaining a sample under borehole-like conditions, wherein said sample is in fluid communication with an ultrasonic source;
 b. nucleating bubbles in said sample by activating said ultrasonic source; and
 c. detecting the onset of bubble formation by measuring one or more sample properties, wherein said sample properties include pressure, volume, temperature acoustic radiation, transit time, amplitude, harmonics, and subharmonics and combinations thereof.

21. The method of claim 20, wherein said ultrasonic source acts as a heat source.

22. An apparatus to determine phase characteristics of a formation fluid, comprising:
 a. means to withdraw a sample under borehole-like conditions having an ultrasonic source, wherein said ultrasonic source is used to nucleate bubbles in said sample;
 b. means to detect the presence of bubbles in said sample by monitoring one or more ultrasonic source properties.

23. The apparatus of claim 22, wherein said ultrasonic source properties are selected from a group consisting of resonance frequency, voltage, voltage squared, current, current squared, phase angle between current and voltage, power dissipation, and electrical impedance, and combinations thereof.

24. The apparatus of claim 22, wherein said ultrasonic source has a roughened surface in contact with said sample.

25. An apparatus to determine phase characteristics of a formation fluid, comprising:
 a. means to withdraw a sample under borehole-like conditions having an ultrasonic source, wherein said ultrasonic source is used to nucleate bubbles in said sample;
 b. means to detect the onset of bubble formation in a sample by monitoring sample properties, wherein said sample properties are selected from a group consisting of compressibility, pressure, volume and temperature, and combinations thereof.

26. The apparatus of claim 25, wherein said ultrasonic source has a roughened surface.

27. The apparatus of claim 25, further comprising a heat source.

28. The apparatus of claim 27, wherein said ultrasonic source acts as said heat source.

29. An apparatus to determine phase characteristics of a formation fluid, comprising:
 a. means to withdraw a sample under borehole-like conditions having an ultrasonic source, wherein said ultrasonic source is used to nucleate bubbles in said sample; and
 b. a receiver to monitor acoustic radiation, transit time, amplitude, harmonics, and subharmonics of said sample.

30. The apparatus of claim 29, wherein said ultrasonic source has a roughened surface.

31. A method of determining phase characteristics of a formation fluid, comprising:
 a. withdrawing a first sample of said formation fluid using a sampling means having an ultrasonic source;
 b. activating said ultrasonic source;
 c. rapidly depressurizing said first sample;
 d. nucleating bubbles in said depressurized first sample using said ultrasonic source;
 e. detecting the onset of bubble formation in said first sample;
 f. estimating the bubble point of said sample based on measurements made in step (e);
 g. purging said first sample;
 h. withdrawing a second sample of said formation fluid;
 i. activating said ultrasonic source;
 j. slowly depressurizing said second sample over a range of pressures deduced from said estimated bubble point;
 k. nucleating bubbles in said depressurized second sample using said ultrasonic source;
 l. detecting the onset of bubble formation in said second sample; and
 m. determining the bubble point pressure of said second sample, wherein said pressure represents the bubble point pressure.

32. The method of claim 31, wherein the step of detecting the onset of bubble formation in said first sample is comprised of: monitoring one or more properties selected from the group consisting of ultrasonic source properties, compressibility, and acoustic properties.

33. The method of claim 32, wherein the step of determining the bubble point pressure of said second sample is comprised of: by monitoring one or more properties selected from the group consisting of ultrasonic source properties, compressibility, and acoustic properties.

* * * * *